(12) United States Patent
Paques et al.

(10) Patent No.: US 9,308,125 B2
(45) Date of Patent: Apr. 12, 2016

(54) APPARATUS FOR INTRA-OCULAR INJECTION

(75) Inventors: Michel Paques, Paris (FR); Pierre Roy, Paris (FR)

(73) Assignees: FOVEA PHARMACEUTICALS, Paris (FR); FONDATION OPHTALMOLOGIQUEADOLPHE DE ROTHSCHILD, Paris (FR)

( * ) Notice: Subject to any disclaimer, the term of this patent is extended or adjusted under 35 U.S.C. 154(b) by 1043 days.

(21) Appl. No.: 12/522,619

(22) PCT Filed: Jan. 9, 2008

(86) PCT No.: PCT/EP2008/050206
§ 371 (c)(1),
(2), (4) Date: Sep. 11, 2009

(87) PCT Pub. No.: WO2008/084064
PCT Pub. Date: Jul. 17, 2008

(65) Prior Publication Data
US 2010/0010452 A1    Jan. 14, 2010

(30) Foreign Application Priority Data

Jan. 9, 2007 (EP) .................................. 07360001
Jan. 9, 2007 (EP) .................................. 07360002

(51) Int. Cl.
*A61M 5/32* (2006.01)
*A61F 9/00* (2006.01)
*A61M 5/42* (2006.01)

(52) U.S. Cl.
CPC ............ *A61F 9/0017* (2013.01); *A61M 5/3287* (2013.01); *A61M 5/427* (2013.01)

(58) Field of Classification Search
CPC .......... A61M 2210/0612; A61M 5/46; A61M 25/0082; A61M 25/0084
USPC ......... 604/181, 187, 192–198, 110, 218–231, 604/232–234, 61–64
See application file for complete search history.

(56) References Cited

U.S. PATENT DOCUMENTS

| 5,266,562 A | 11/1993 | Mukherjee et al. |
| 5,358,491 A | 10/1994 | Johnson et al. |
| 5,770,589 A | 6/1998 | Billson et al. |
| 6,299,603 B1 * | 10/2001 | Hecker ................... A61F 9/007 604/181 |
| 6,309,374 B1 | 10/2001 | Hecker et al. |
| 6,638,255 B1 * | 10/2003 | Weber ................. A61M 5/3129 604/181 |

(Continued)

FOREIGN PATENT DOCUMENTS

| FR | 2842112 A | 1/2004 |
| WO | WO-00/07530 A | 2/2000 |
| WO | WO-01/49226 A | 7/2001 |

OTHER PUBLICATIONS

Martin Remington's Pharm. Sci., 15th Ed. (Mack Publ. Co., Easton (1975)).

*Primary Examiner* — Phillip Gray
(74) *Attorney, Agent, or Firm* — Jeremy P. Bond

(57) ABSTRACT

The present technology relates to an apparatus for intraocular injection comprising a plate adapted for being brought into contact with an eye and a guide operable to guide a needle into the interior of an eye, characterized in that it comprises means for displacing a superficial layer (1) of the eye over an underlying layer (2) of the eye as the plate is brought into contact with the eye before the needle is guided into the interior of the eye.

35 Claims, 22 Drawing Sheets

(56) References Cited

U.S. PATENT DOCUMENTS

| | | |
|---|---|---|
| 6,693,125 B2 | 2/2004 | Borisy et al. |
| 6,746,429 B2 * | 6/2004 | Sadowski ............ A61M 5/2425 604/198 |
| 6,846,816 B2 | 1/2005 | Borisy et al. |
| 6,897,206 B2 | 5/2005 | Sackeyfio et al. |
| 6,955,815 B2 | 10/2005 | Sackeyfio et al. |
| 2001/0008961 A1 | 7/2001 | Hecker et al. |
| 2003/0060763 A1 | 3/2003 | Penfold et al. |
| 2006/0047250 A1 | 3/2006 | Hickingbotham et al. |
| 2006/0161114 A1 | 7/2006 | Perot et al. |
| 2006/0271025 A1 * | 11/2006 | Jones ................ A61F 9/00802 606/4 |

* cited by examiner

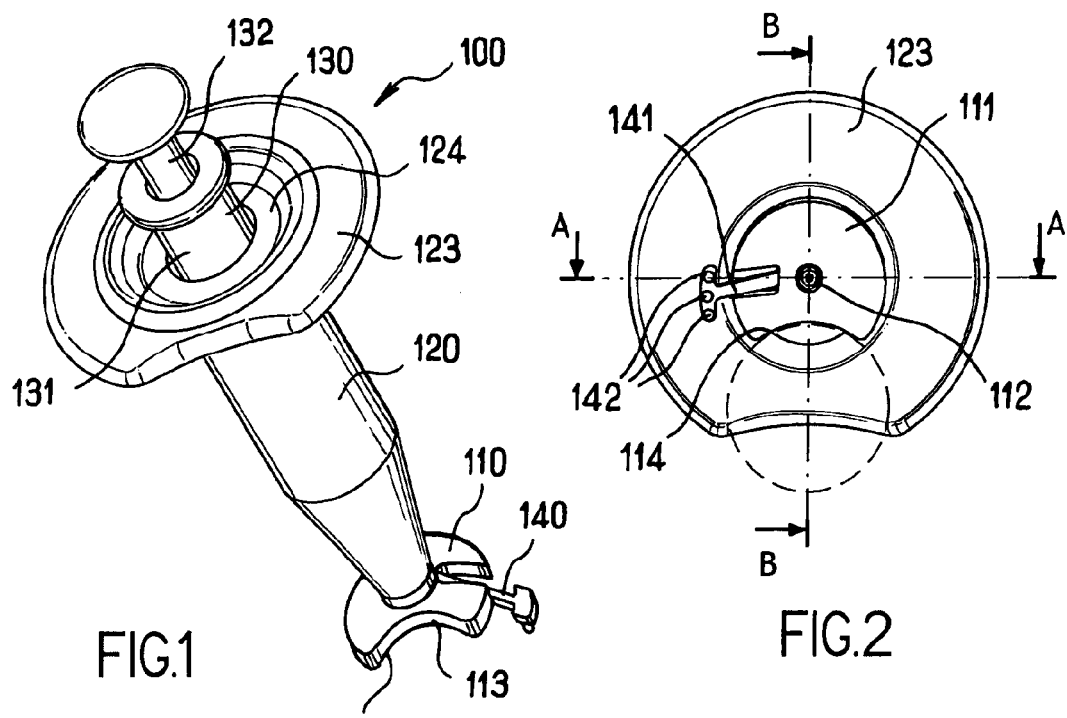
FIG.1
FIG.2
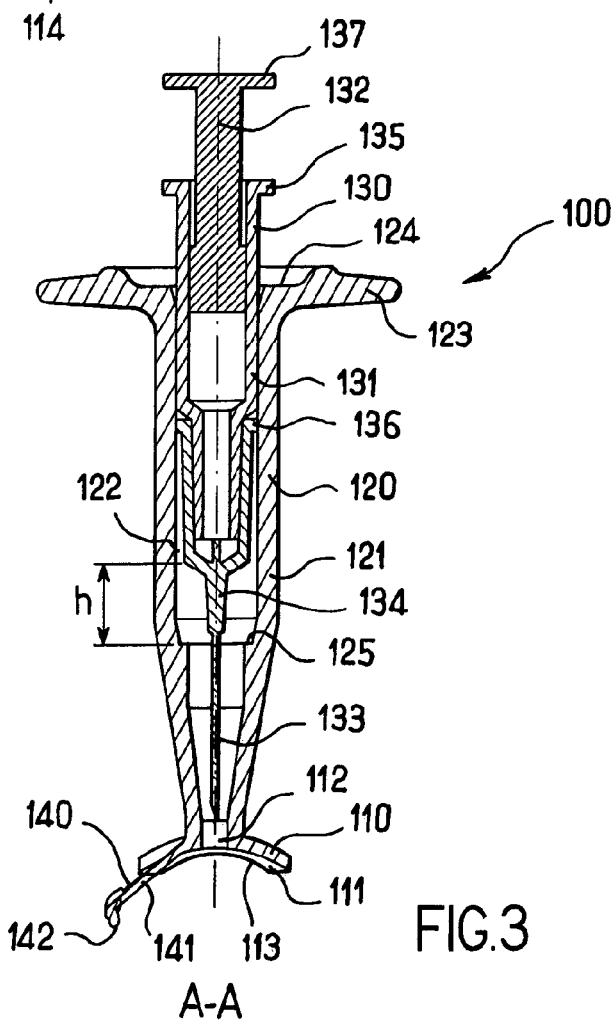
FIG.3
A-A

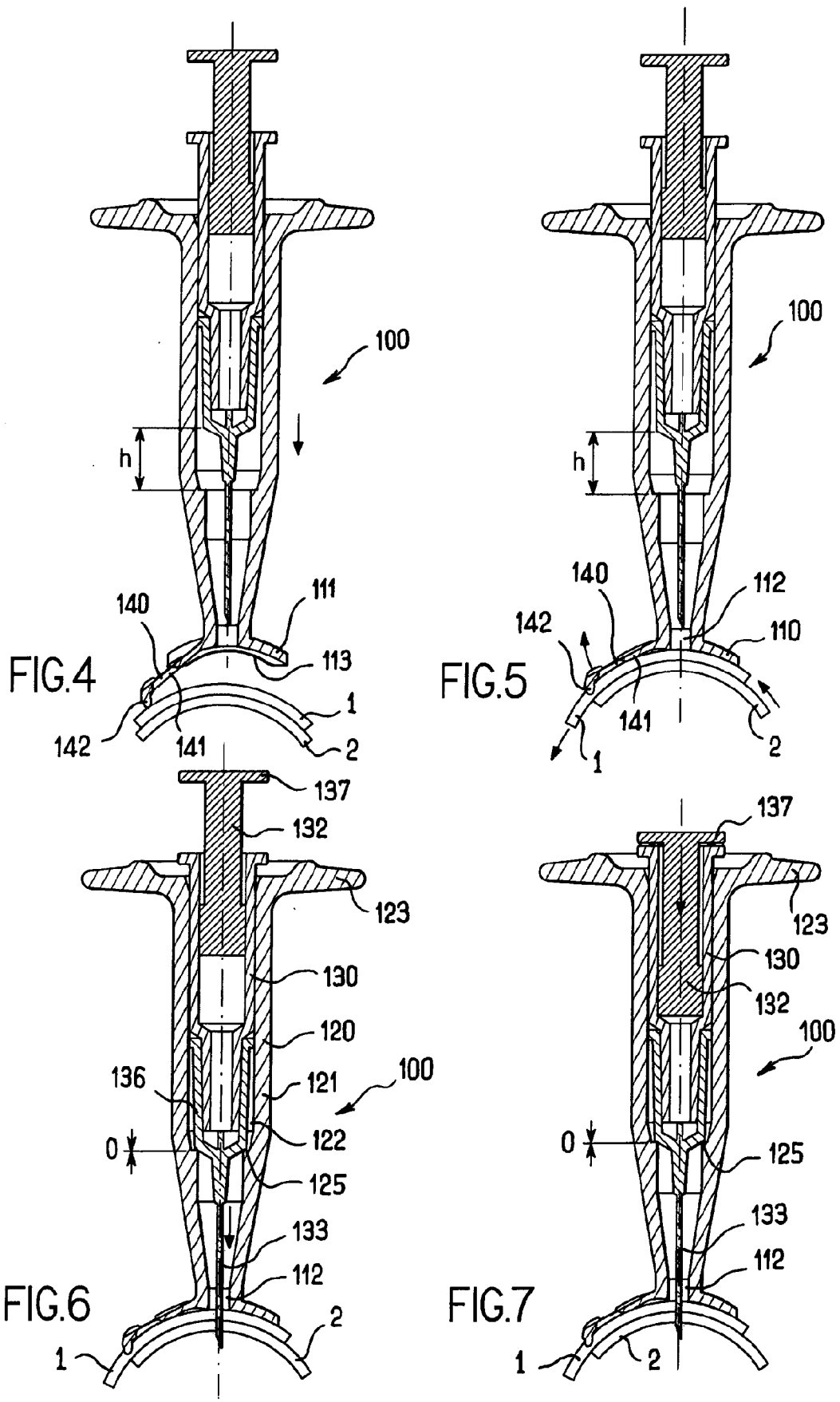

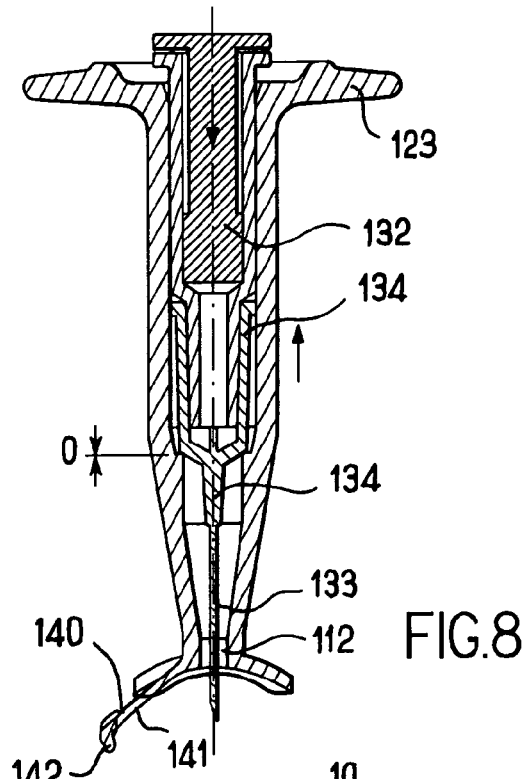
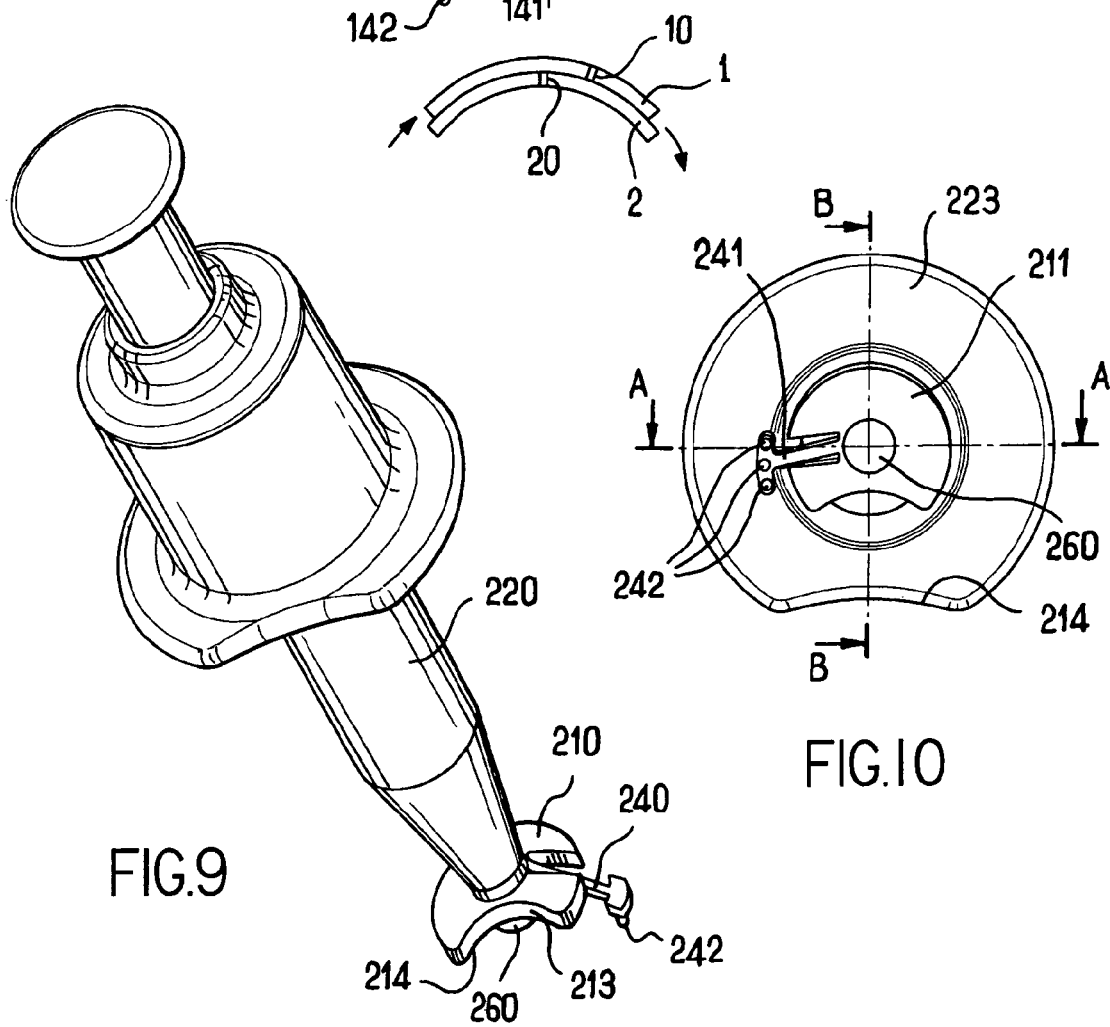

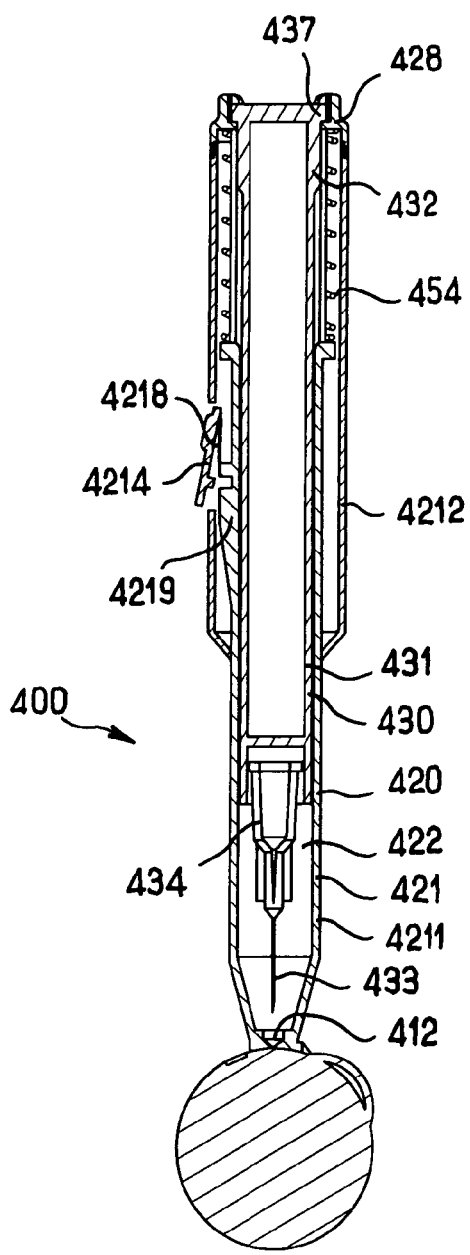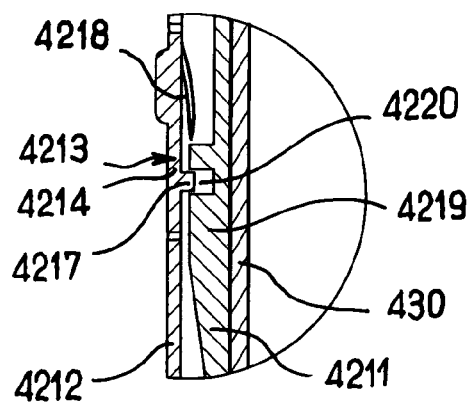
FIG. 27
FIG. 30

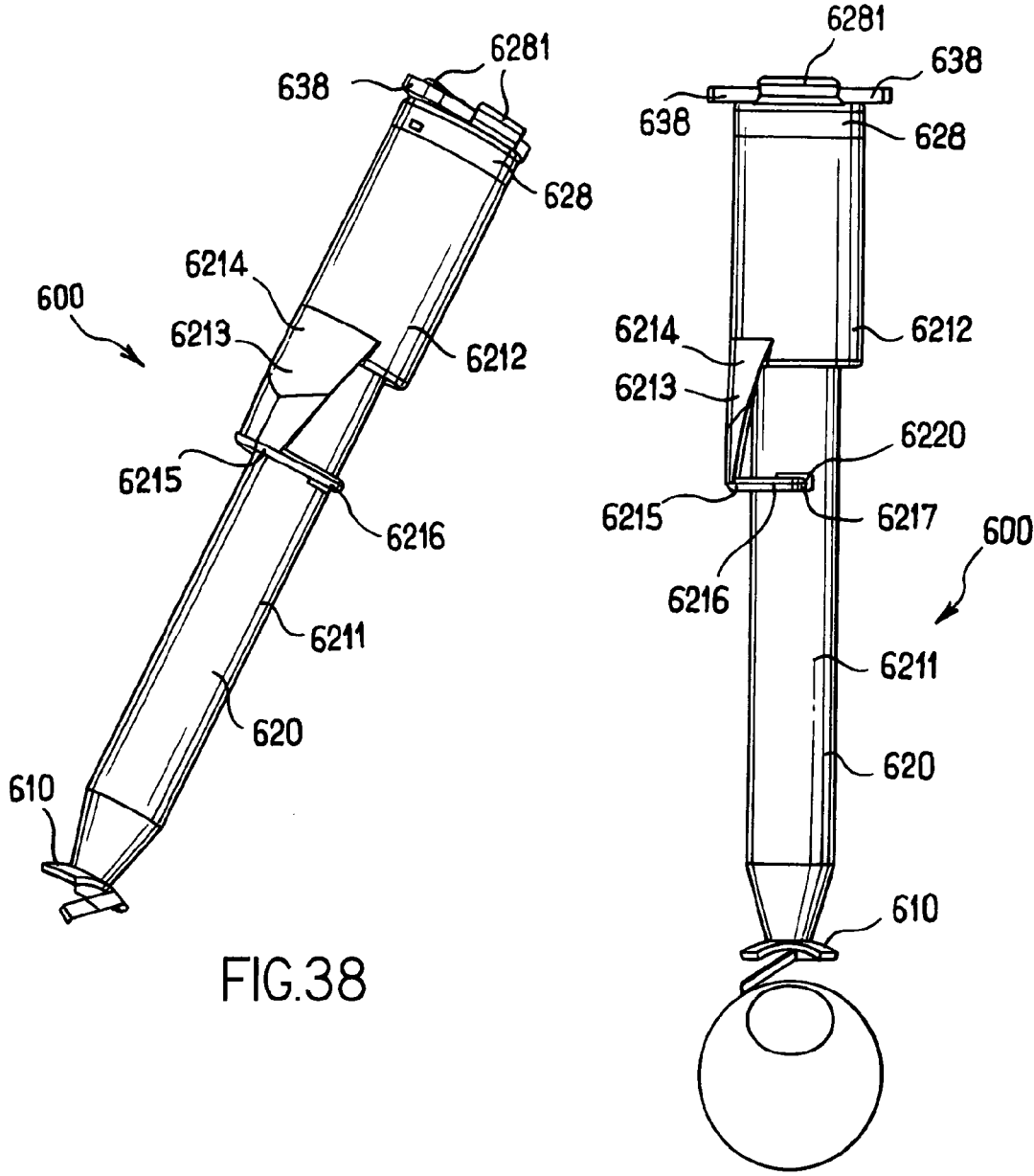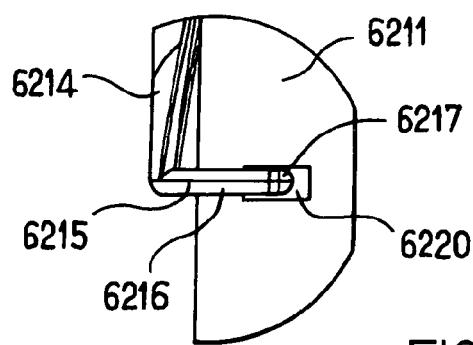
FIG.38
FIG.39
FIG.40

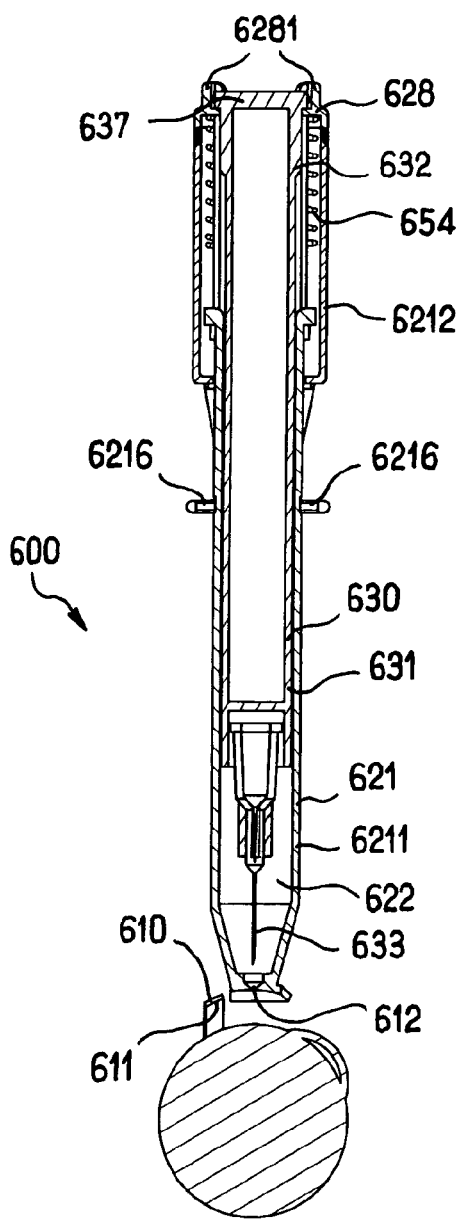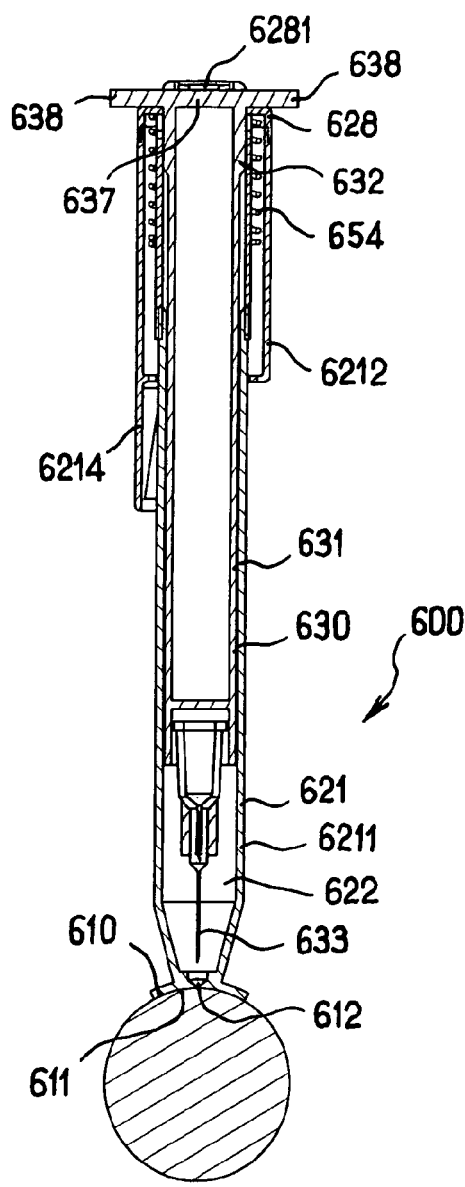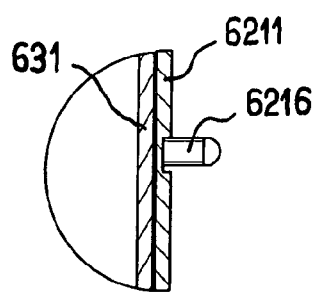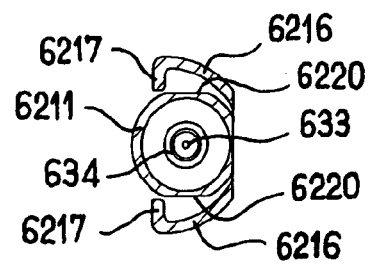

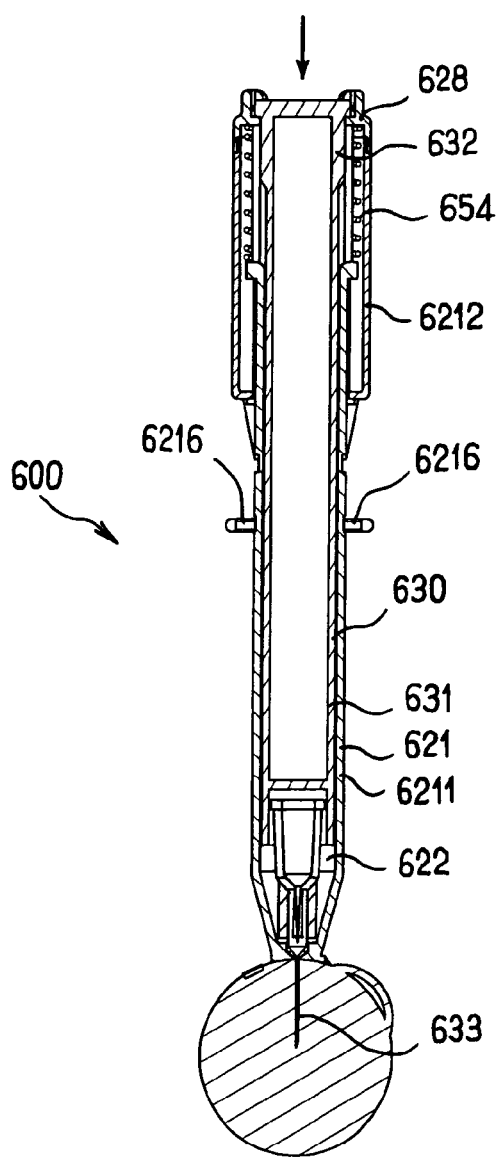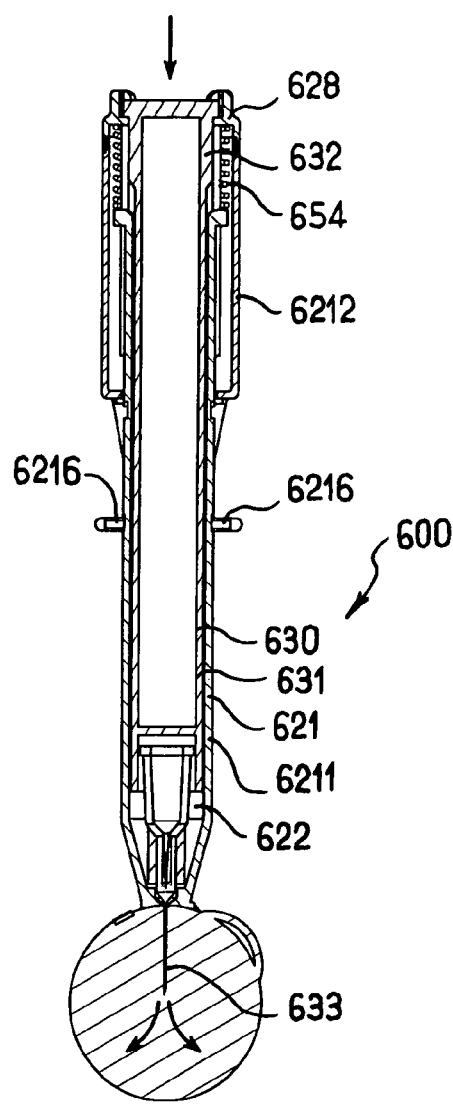
FIG. 43   FIG. 44
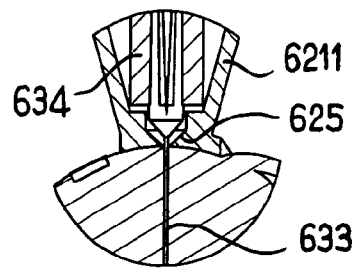
FIG. 47

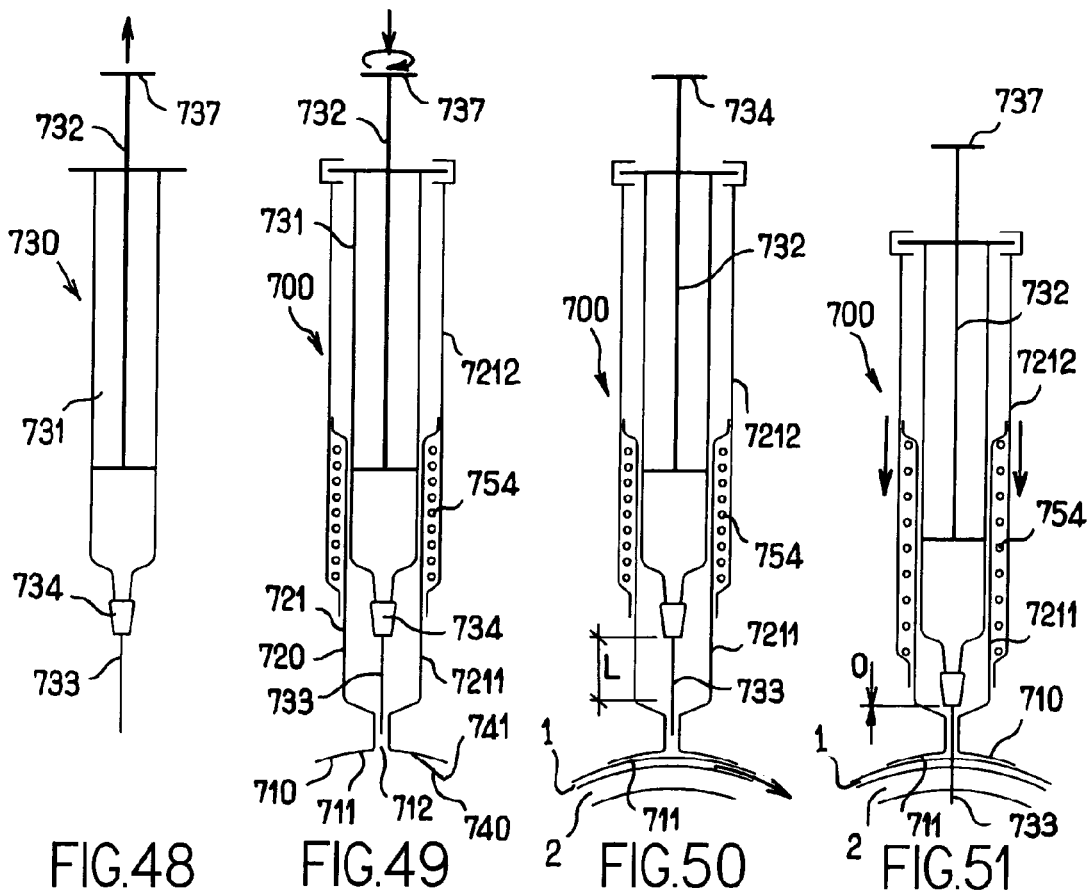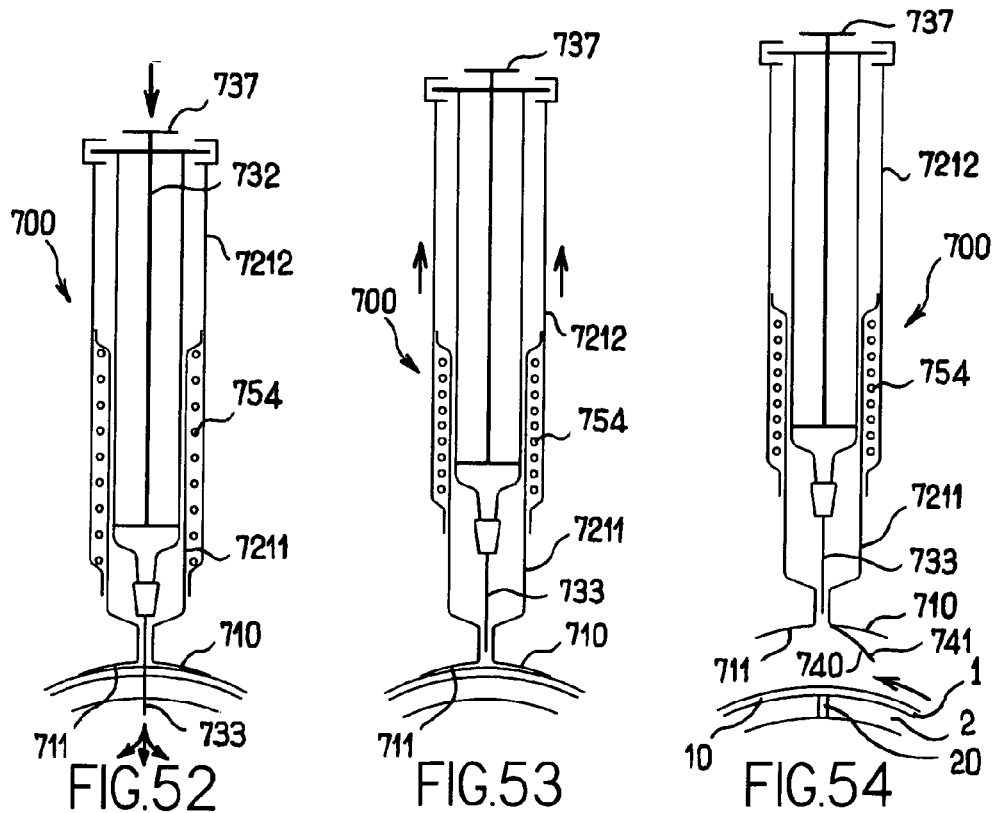
FIG.48  FIG.49  FIG.50  FIG.51  FIG.52  FIG.53  FIG.54

APPARATUS FOR INTRA-OCULAR INJECTION

CROSS-REFERENCE TO RELATED APPLICATIONS

This application is a National Phase Entry of International Application No. PCT/EP2008/050206, filed on Jan. 9, 2008, which claims priority to European Application No. 07360002.5, filed on Jan. 9, 2007 and European Application No. 07360001.7, filed Jan. 9, 2007, all of which are incorporated by reference herein.

BACKGROUND

The present invention relates to apparatus and methods for treating eyes, such as eyes of mammals having eye disorders or diseases, more particularly to apparatus and methods for administering a therapeutic medium or agent intravitreously, yet more particularly to apparatus and methods for administering such therapeutics or agents to the tissues of the eye so that the pharmaceutical action of the such therapeutics/agents is localized at the choroid and the retina, or at the ciliary body or the lens.

There are a number of vision-threatening disorders or diseases of the eye of a mammal including, but not limited to diseases of the retina, retinal pigment epithelium (RPE), ciliary body, lens and choroid. Such vision threatening diseases include, for example, ocular neovascularization, ocular inflammation and retinal degenerations. Specific examples of these disease states include diabetic retinopathy, glaucoma, chronic glaucoma, posterior capsule opacification, retinal detachment, sickle cell retinopathy, age-related macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy and lensectomy, vascular diseases, retinal ischemia, choroidal vascular insufficiency, choroidal thrombosis, neovascularization of the optic nerve, diabetic macular edema, cystoid macular edema, macular edema, retinitis-pigmentosa, retinal vein occlusion, proliferative vitreoretinopathy, angioid streak, and retinal artery occlusion, and, neovascularization due to penetration of the eye or ocular injury.

A number of techniques or methodologies have been developed to deliver drugs to the various eye tissues or structure to treat a wide range of these disorders or diseases. However, delivery of drugs, proteins and the like to the eye(s) of mammals so as to achieve the desired therapeutic or medical effect, especially to the retina and/or the choroids, has proven to be challenging, most of which is owed to the geometry, delicacy and/or behavior of the eye and its components. A brief description of various conventional methods or techniques for delivering drugs to the tissues of the eye and the shortcomings thereof are hereinafter described.

Oral ingestion of a drug or injection of a drug at a site other than the eye can provide a drug systemically however such a systemic administration does not provide effective levels of the drug specifically to the eye. In many ophthalmic disorders involving the retina, posterior tract, and optic nerve, adequate levels of the drug cannot be achieved or maintained by oral or parenteral routes of administration. Thus, further and repeated administration of the drug would be necessary to achieve the desired or adequate levels of concentration of the drug. Such further and repeated administrations of such drugs, however, may produce undesired systemic toxicity.

Ophthalmic conditions have also been treated using drugs applied directly to the eye in either liquid or ointment form. This route of administration (i.e., topical administration), however, is only effective in treating problems involving the superficial surface of the eye and diseases that involve the cornea and anterior segment of the eye, such as for example, conjunctivitis. Topical administration of drugs is ineffective in achieving adequate concentrations of a drug(s) in the sclera, vitreous, or posterior segment of the eye. In addition, topical eye drops may drain from the eye through the nasolacrimal duct and into the systemic circulation, further diluting the medication and risking unwanted systemic side effects. Furthermore, delivery of drugs in the form of topical eye drops is also of little utility because the drug cannot cross the cornea and be made available to the vitreous, retina, or other subretinal structures such as the retinal pigment epithelium ("RPE") or choroidal vasculature and/or is highly unstable and therefore not easily formulated for topical delivery. Moreover, data also indicates that it is not unusual for up to 85% of topically applied agents to be removed by the eye's blink mechanism/reflex.

Direct delivery of drugs to the eye by a topical insert has also been attempted however this method is not desirable. Such topical inserts require patient self-administration and thus education on their insertion into and removal from the eye. Consequently, this technique demands a certain degree of manual dexterity that can be problematic for geriatric patients who are particularly susceptible to certain eye disorders that appear age related (e.g., age related macular degeneration). Also, in many instances such topical inserts may cause eye irritation and such inserts are prone to inadvertent loss due to eyelid laxity. In addition, these devices provide a source of drug only to the cornea and anterior chamber, and thus do not provide any pharmacologic advantage over topical eye drops or ointments. Thus, such devices have limited, if any at all, utility for providing an effective source of drugs to the vitreous or tissues located in the posterior segment of the eye.

As a consequence most methods for treating eye disorders or diseases in the posterior segment, or the back-of-the-eye, involve intraocular (and more specifically intravitreal) delivery of the drug. One such technique for intravitreal delivery is accomplished by intraocular injection of the drug or microspheres containing the drug directly into the vitreous or by locating a device or capsule containing the drug in the vitreous, such as that described in U.S. Pat. No. 5,770,589.

Intraocular injection is commonly used in ophthalmology for delivering therapeutics or agents (e.g. drugs of interest) to the posterior segment of the eye, especially when it is useful to deliver high concentrations of drugs. Such an operation is used in particular for injecting compositions comprising for example corticosteroids or neovascularization inhibitors in the vitreous body of the eye, in order to treat diseases affecting retina or choroids, or ciliary body or lens.

Intraocular injection procedure generally consists in:
  moving apart the eyelids with an eyelids retractor,
  locating an injection area on the eye using a compass,
  introducing the needle into the eye at the level of the injection area, and
  injecting a composition via the needle and removing the needle while pressing the superficial layers of the eye in the injection area in order to limit the risk of leakage of the injected substance.
Such a procedure requires high technical skills and lots of practice. For this reason, many non-qualified ophthalmologists are not able to carry out such operations.

In particular, the injection area must be precisely defined. In order to avoid damaging structures located in front of the vitreous body (such as cornea, iris and lens crystalline) and structures located at the rear of the vitreous body (such as retina), the needle is generally introduced at a given distance, usually around 3 to 4 mm, from the limbus zone, which is a transition zone extending between the cornea and the sclera. The depth of penetration of the needle into the eye must also be carefully controlled.

Additionally, precautions must be taken in order to limit risks of complications due to perforation of eye tissues. In particular, perforation of the tissues can cause leakage of the injected composition out of the eye though the orifice created by the needle. This phenomenon prevents the ophthalmologist from controlling the amount of active compound that has been actually introduced into the eye. Moreover, perforation of the tissues can also favour penetration of germs into the eye, causing ocular infections.

Document WO 01/49226 discloses an apparatus for facilitating intraocular injection, comprising a plaque which is adapted to be positioned over an eye of a patient so as to be centred on the iris. The plaque has apertures for guiding a syringe needle into the eye. The inner surface of the plaque which contacts the eye is equivalent to the exposed surface of the eye when substantially open. This document mentions that the positioning of the plaque may be aided for example by a ring on the plaque showing the border between the iris and the sclera.

However, such an apparatus is not very easy to handle, as the ophthalmologist must maintain the apparatus with one hand while operating the syringe with the other hand. Moreover, in such an apparatus, the plaque is necessarily bulky, as it must covers all the exposed surface of the eye. And the positioning of such an apparatus necessitates that the eyelids be retracted. And finally, as the plaque is centred on the iris, the apparatus is not adapted to an eye having a cornea of non-standard diameter.

SUMMARY

It is an object of the invention to provide an apparatus for intraocular injection which would be easy to handle. It is another object of the invention to limit the risks of leakage of injected the composition and penetration of germs into the eye.

This problem is solved according to the invention thanks to an apparatus according to claim 1. By displacing a superficial layer of the eye over an underlying layer of the eye, the layers are shifted one relative to the other, so that the needle pierces the layers in two different zones. When the apparatus is removed from the eye, the superficial layer comes back to its initial position, thereby closing the orifice created by the needle in the underlying layer. The composition which has been injected into the eye is prevented from leaking out of the eye. Moreover, this also avoids penetration of germs into the eye.

BRIEF DESCRIPTION OF THE DRAWINGS

The invention will be described with reference to the drawings, in which:

FIG. 1 is a three-dimensional schematic view of an apparatus for intra-ocular injection according to a first embodiment of the invention;

FIG. 2 is a bottom view of the apparatus of FIG. 1;

FIG. 3 is a cut-away view of the apparatus of FIGS. 1 and 2;

FIGS. 4 to 8 illustrate different steps of a method for performing intra-ocular injection using the apparatus of FIGS. 1 to 3;

FIG. 9 is a three-dimensional schematic view of an apparatus for intra-ocular injection according to a second embodiment of the invention;

FIG. 10 is a bottom view of the apparatus of FIG. 9;

FIG. 18 is a cut-away view of the apparatus of FIGS. 16 and 17;

FIGS. 25 to 29 are cut-away views illustrating different steps of a method for performing intra-ocular injection using the apparatus of FIGS. 23 and 24;

FIG. 30 is an enlarged view showing a detail of FIG. 27;

FIGS. 38 and 39 are three-dimensional schematic views of an apparatus for intra-ocular injection according to a sixth embodiment of the invention;

FIG. 40 is an enlarged view showing a detail of FIG. 39;

FIGS. 41 to 44 are cut-away views illustrating different steps of a method for performing intra-ocular injection using the apparatus of FIGS. 38 and 39;

FIG. 45 is an enlarged view showing a detail of FIG. 41;

FIG. 46 is a sectional cut-away view of the apparatus in the position represented on FIG. 42;

FIG. 47 is an enlarged view showing a detail of FIG. 44;

FIGS. 48 to 54 are schematic cut-away views illustrating different steps of a method for performing intra-ocular injection using an apparatus according to a seventh embodiment of the invention;

DETAILED DESCRIPTION

Figure 11:
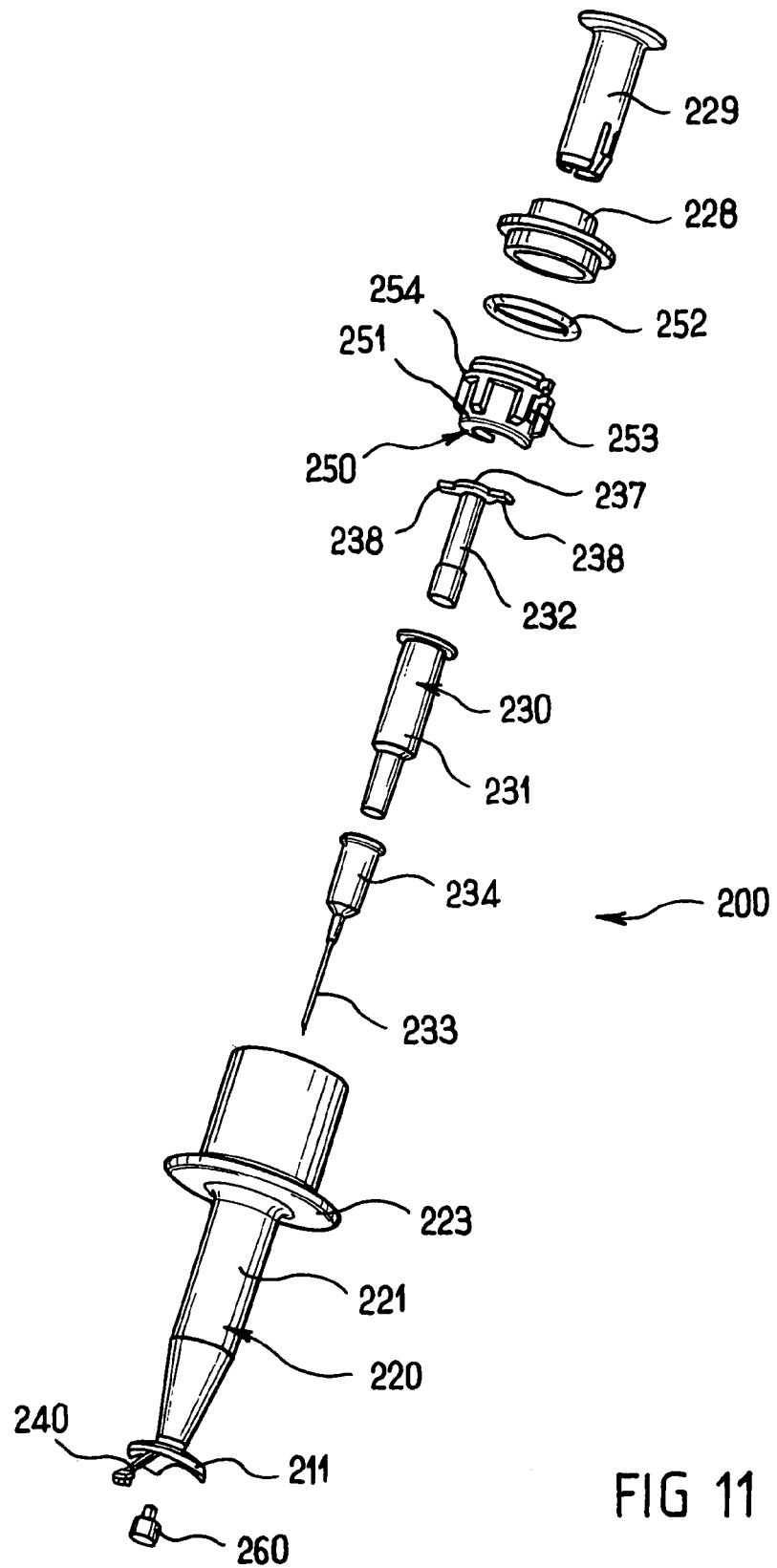
FIG. 11 is an exploded view of the apparatus of FIGS. 9 and 10.

FIGS. 1 to 3 illustrate an apparatus 100 for intra-ocular injection according to a first embodiment of the invention. The apparatus 100 comprises a plate 110 adapted for being brought into contact with an eye, a support 120 for receiving a syringe and optionally a syringe 130. The plate 110 has an eye bearing surface 111 having a curved shape for matingly bearing on the outer surface of the eye and an aperture 112 provided in the plate 110 for allowing a needle to pass through the plate 110. Moreover, the plate 110 has a cut-out 113 having an edge 114 with a curved shape. More precisely, the edge of the cut-out has a substantially circular shape which corresponds to a shape of a limbus (as shown in dotted line on FIG. 2) so that the edge 114 can be superimposed on the limbus. The cut-out 113 has a diameter of about 12 millimeters.

The cut-out serves as a reference for precisely positioning the apparatus with respect to the eye in order to perform an intra-ocular injection. The cut-out 113 is provided in the plate 111, such that when the cut-out is superimposed on the limbus, the aperture 112 is located at a distance of about 3.5 millimeters from the limbus.

The support 120 comprises a hollow body 121 extending over the aperture 112. The hollow body 121 comprises an inner guiding channel 122. The inner guiding channel 122 extends between a first open end opening onto the aperture 112 and a second open end for introduction of the syringe 130 into the channel 122. The inner guiding channel 122 is of cylindrical shape and is adapted for receiving the syringe 130 in such a way that the syringe 130 can slide into the guiding channel 122.

According to one special embodiment, the syringe 130 is optional and is not present in the apparatus of the present invention. According to this special embodiment, the said syringe 130 is inserted in the inner guiding channel 122 before use of the said apparatus for administering compound or composition of interest (i.e. the therapeutic medium) into the eye as disclosed herein.

According to a preferred embodiment, the support 120 comprises an annular flange 123 provided near the second open end of the channel 122. The annular flange 123 projects outwardly from the body 121, in a radial direction relative to the axis of the guiding channel 122. The annular flange 123 allows an operator to retain the support when sliding the syringe 130 relative to the body 121.

According to a preferred embodiment, the support 120 also comprises a first bearing surface 124 against which a rim of the syringe barrel can abut. The bearing surface 124 is substantially flat, has an annular shape and extends in a radial direction relative to the axis of the guiding channel 122. In the example of FIG. 3, the bearing surface 124 is arranged in a recess provided in the annular flange 123.

Moreover, the support 120 comprises a second bearing surface 125 against which a rim of a needle support can abut. The bearing surface 125 is formed by a shoulder in the guiding channel 122.

The syringe 130 comprises a syringe barrel 131 having a cavity for containing a composition (e.g. the therapeutic medium) to be injected into an eye, a syringe plunger 132 which can slide into the syringe barrel 131 in order to push the composition out of the syringe, a syringe needle 133 for carrying the composition from the syringe barrel to the interior of the eye and a needle support 134 for securing the needle to the barrel 131. The syringe support 134 is moulded over the needle 133.

The guiding channel 122 has an inner diameter which corresponds to the outer diameter of the syringe barrel 130, so that the syringe is guided into the support 120.

The syringe barrel 131 has an annular rim 135 which can abut against the bearing surface 124 for limiting the sliding movement of the syringe into the guiding channel 122. According to preferred embodiment, the needle support 134 also has an annular rim 136 which can abut against the bearing surface 125 for limiting penetration of the needle 133 into the eye.

And in a known manner, the plunger 132 has an enlarged part 137 which is used by an ophthalmologist to apply a pressure on the plunger 132 in order to make it slide into the barrel 130. The enlarged part 137 can abut against the syringe barrel 131 for limiting the sliding movement of the syringe plunger 132 into the syringe barrel 130.

On FIGS. 1 to 3, the syringe is represented in a retracted position, in which the needle 133 extends inside the hollow body 121.

The apparatus 100 also comprises a resilient member 140 for displacing a superficial layer of the eye over an underlying layer of the eye. The resilient member 140 comprises a flexible leg 141 projecting outwardly from the plate 110 from the side of the bearing surface 111 and a plurality of teeth 142 arranged at the free end of the flexible leg 141.

The flexible leg 141 extends in a direction substantially tangential with respect to the edge 114 of the cut-out 113.

According to preferred embodiment, the plate 110, the support 120 and the resilient member 140 are made in one piece. The resilient member 140 is preferably made of an hydrophobic material, especially in order to maximize the grip of the resilient member on the conjunctiva. In this first embodiment, the apparatus 100 can be used with a standard syringe. It should be noticed that the said syringe 130 can be of various origin, such as commercially pre-filed syringe, syringe widely provided commercially, etc.

FIGS. 4 to 8 illustrate different steps of a method for performing intra-ocular injection using the apparatus 100. According to a first step (FIG. 4), the ophthalmologist bring the apparatus 100 into contact with an eye. During this step, the resilient member 140 comes first into contact with the eye. More precisely, the teeth 142 provided a free end of the flexible leg 141 engage a superficial layer 1 of the eye (called "conjunctiva") extending over an underlying layer 2 (called "sclera"). The teeth 141 engage the superficial layer 1 in a zone where the superficial layer 1 is mobile relative to the underlying layer 2 (i.e. around the limbus) and where the layers of the eye are compact.

Moreover, while the apparatus 100 is moved toward the eye, the flexible leg 141 is urged against the superficial layer 1. As a consequence, the flexible leg 141 is bent and applies a tangential force to the superficial layer 1. As result, the superficial layer 1 (conjunctiva), which is mobile with respect to the underlying layer 2 (sclera), slides over the underlying layer 2. The superficial layer 1 is shifted about 1 to 2 millimeter relative to the underlying layer 2 in a direction substantially tangential to the limbus.

According to a second step (FIG. 5), the ophthalmologist brings the plate 110 into contact with the superficial layer 1. The plate 110 is positioned over the eye so that the edge of the cut-out 113 is superimposed on the limbus delimiting the cornea and the sclera of the eye. In such a position of the apparatus, the aperture 112 is situated at a distance of about 3.5 millimeters from the limbus.

According to a third step (FIG. 6), the ophthalmologist apply a pressure on the syringe plunger 132. As a consequence, the syringe 130 slides into the guiding channel 122 from a retracted position to an injection position in which the needle 133 protrudes out of the body 121 through the aperture 112. During the movement of the syringe, the needle 133 penetrates into the eye through the different layers 1, 2 of the eye until the tip of the needle reaches the vitreous body of the eye.

The sliding movement of the syringe is stopped by the needle support 134 coming into abutment against the second bearing surface 125. The second bearing surface 125 is arranged such that the stroke of the syringe is h, in order that the needle 133 penetrates into the eye at a depth of about 3 to about 10 millimeters (e.g. 6 millimeters).

By limiting the stroke of the needle 133, the second bearing surface 125 prevents the needle from damaging intraocular structures such as the retina or lens.

According to a fourth step (FIG. 7), the ophthalmologist carry on applying a pressure on the plunger 132. As a consequence, the plunger 132 slides into the barrel 131, whereby the composition is pushed out of the barrel 131 and injected into the eye via the needle 133.

The third and fourth steps are performed successively while the ophthalmologist is continuously applying a pressure on the plunger 132. This is due to the fact that the force required for moving the syringe 130 relative to the body 121 is lower than the force required for moving the plunger 132 relative to the barrel 131.

According to a fifth step (FIG. 8), the apparatus 100 is removed from the eye. Thus the resilient member 140 is moved away from the eye. As a consequence, the superficial layer 1 slide over the underlying layer 2, back to its initial position. The orifice 10 created in the superficial layer 1 by the needle 133 is shifted relative to the orifice 20 created in the underlying layer 2. As the orifice 20 is obstructed by the superficial layer 1, the composition which has been injected into the vitreous body of the eye is prevented from leaking out of the eye. Moreover, this also avoids penetration of germs into the eye.

FIGS. 10 to 13 illustrate an apparatus 200 for intra-ocular injection according to a second embodiment of the invention. The apparatus 200 is similar to the apparatus 100, except that it comprises releasable connecting means 250 for connecting the syringe plunger and the syringe barrel. The apparatus 200 comprises a plate 210, a support 220 and a syringe 230. The plate 210 has an eye bearing surface 211, an aperture 212 and a cut-out 213 having an edge 214.

The support 220 comprises a hollow body 221 extending over the aperture 212 and comprising an inner guiding channel 222 adapted for receiving the syringe 230 in such a way that the syringe 230 can slide into the guiding channel 222. The support 220 comprises an annular flange 223 which projects outwardly from the body 221, in a radial direction relative to the axis of the guiding channel 222. The annular flange 223 allows an operator to retain the support when sliding the syringe 230 relative to the body 221.

The support 220 also comprises a bearing surface 224 against which a rim of the syringe barrel can abut. The bearing surface 224 is substantially flat, has an annular shape and extends in a radial direction relative to the axis of the guiding channel 222. The syringe 230 comprises a syringe barrel 231, a syringe plunger 232, a syringe needle 233 and a needle support 234.

Figure 12:
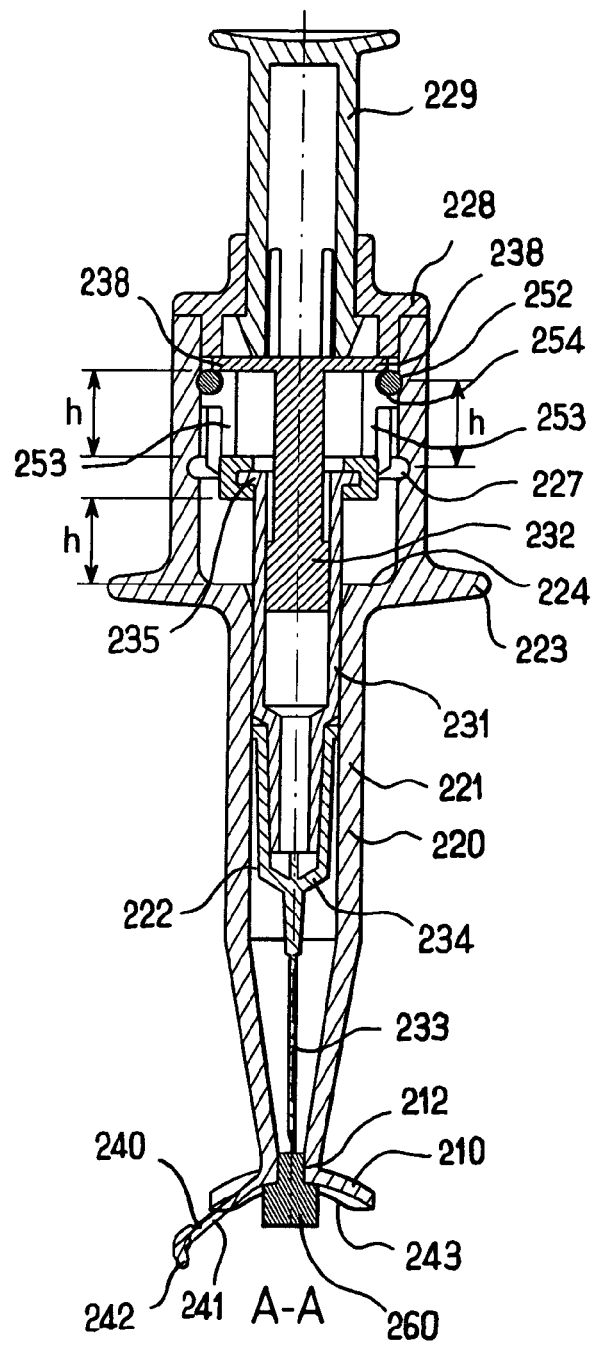
FIGS. 12 and 13 are cut-away views of the apparatus of FIGS. 9 to 11.
Figure 13:
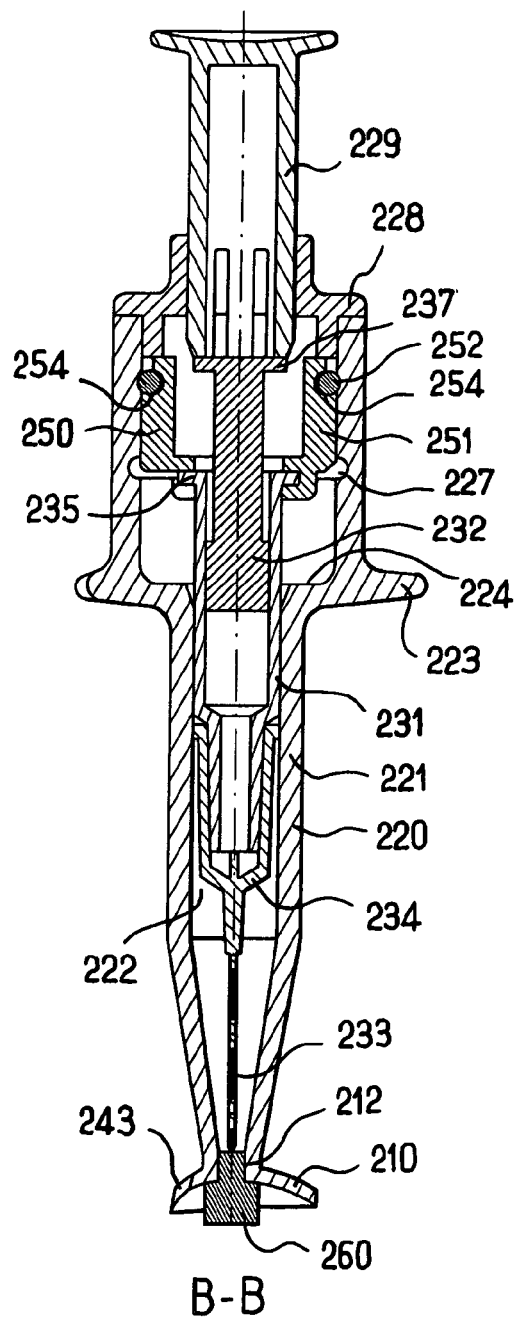

On FIGS. 12 to 13, the syringe is represented in a retracted position, in which the needle 233 extends inside the hollow body 221. According to this second embodiment, the syringe plunger 232 comprises two fingers 238 extending in two opposite radial directions from the enlarged part 237

Moreover, according to this second embodiment, the apparatus 200 comprises a spacer 251 and an elastic open ring 252 arranged between the syringe barrel 231 and the syringe plunger 232 to prevent sliding movement of the plunger relative to the barrel. The spacer 251 has a generally cylindrical shape. The spacer 251 comprises two opposite longitudinal grooves 253 and an annular radial rim 254. Each groove is 253 is adapted for receiving a finger 238 of the plunger 232 so that the finger can slide in the associated groove.

Moreover, when the apparatus 200 is in a retracted position, the elastic open ring 252 is prestressed in the hollow body 221. The elastic open ring 252 extends around the spacer 251 and is interposed between the fingers 238 of the plunger 232 and the rim 254 thereby preventing the fingers 238 from sliding in the grooves 253.

The support 220 comprises a housing 227 in the form of an annular groove provided in the internal surface of the guiding channel 222. The housing is adapted for accommodating the elastic ring when the apparatus is brought to the injection position.

The support 220 also comprise a lid 228 for maintaining the syringe 230, the spacer 251 and the elastic ring 252 inside the guiding channel 222, and a push button 229 which can be operated for applying a pressure on the plunger 232.

Finally, the apparatus 200 comprises a removable cap 260 which is positioned in the aperture 212 for protecting the syringe 230 located inside the hollow body 221 and for preventing the syringe 230 to slide relative to the support 220 by accident. The cap 260 must be removed before operating the apparatus 200. The apparatus 200 is intended to be used in the same way as the apparatus 100 for performing an intraocular injection (FIGS. 4 to 8).

Figure 14:
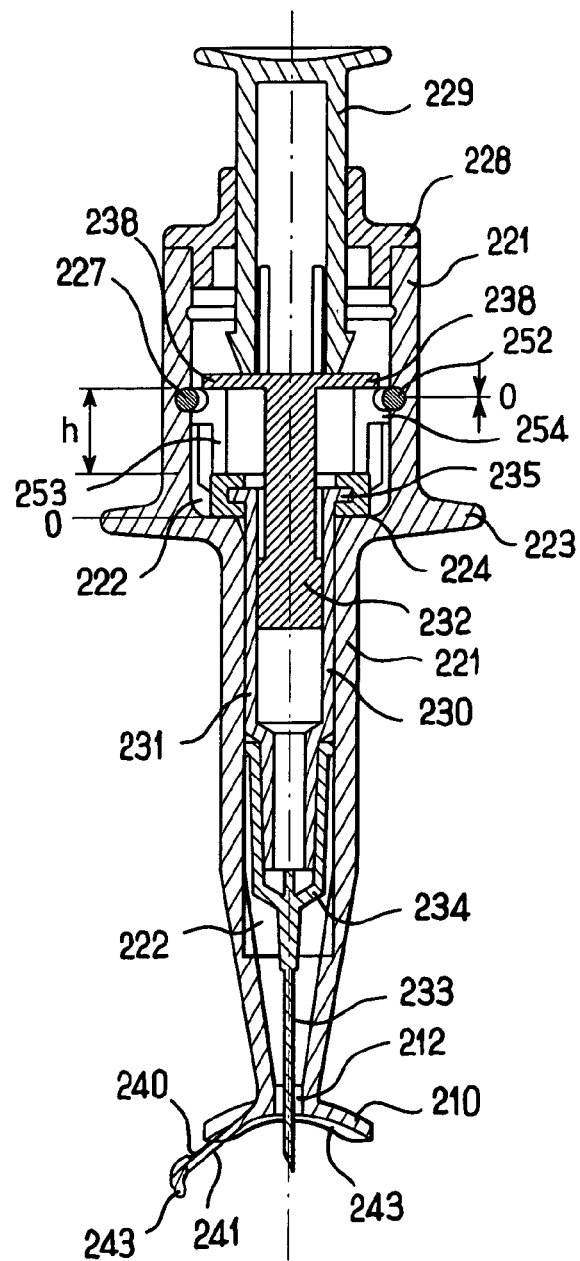
FIGS. 14 and 15 are cut-away views showing the kinematics of the apparatus of FIGS. 9 to 13.
Figure 15:
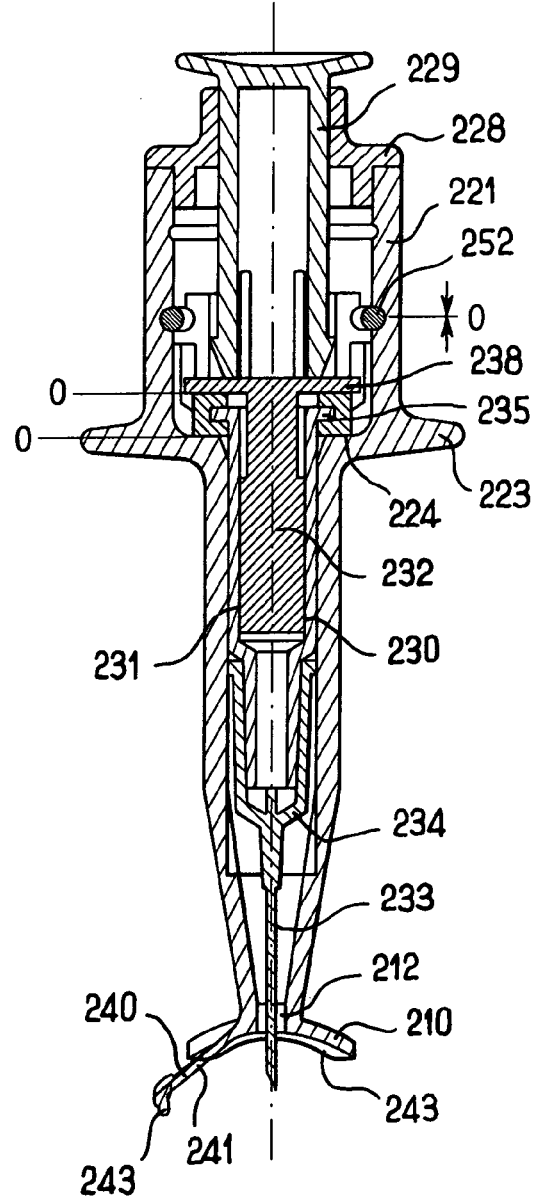

FIGS. 14 and 15 illustrate the kinematics of the apparatus 200 when the ophthalmologist applies a pressure on the push button 229. During a first phase (FIG. 14), the push button 229 presses on the enlarged part 237 of the plunger 232. As the spacer 251 and the elastic ring 252 prevent relative movement between the plunger 232 and the barrel 231, the syringe plunger 232 and a syringe barrel 231 are caused to move in a common sliding movement relative to the body 221. As a consequence, the syringe 230 slides relative to the body 221 towards the injection position until the rim 235 of the barrel 231 abuts against the bearing surface 224 of the body 221.

Moreover, the elastic ring 252 is caused to slide into the guiding channel 222 until the elastic ring 252 reaches the housing 227. Then the elastic ring 252 expands and fits into the housing 227, whereby the connection between the plunger 232 and the barrel 231 is automatically released.

During a second phase (FIG. 15), the push button 229 continues to press on the enlarged part 237 of the plunger 232. As the elastic ring 252 has been withdrawn in the housing 227, the fingers 238 are free to slide into the grooves 253 of the spacer 251. As a consequence, the plunger 232 slides into the barrel 231. The releasable connecting means 250 allows to sequentially slide the syringe towards the injection position and then slide the plunger relative to the barrel, in one gesture, by simply exerting a pressure on the push-button 229.

FIGS. 16 to 22 illustrate an apparatus 300 for intra-ocular injection according to a third embodiment of the invention. The apparatus 300 is similar to the apparatus 200, except that it comprises a carpule and a removable safety ring for preventing movement of the needle relative to the body. The apparatus 300 comprises a plate 310, a support 320 and a syringe 330. The plate 310 has an eye bearing surface 311, an aperture 312 and a cut-out 313 having an edge 314.

The support 320 comprises a hollow body 321 extending over the aperture 312 and comprising an inner guiding channel 322 adapted for receiving the syringe 330 in such a way that the syringe 330 can slide into the guiding channel 322. The support 320 comprises an annular flange 323 which projects outwardly from the body 321, in a radial direction relative to the axis of the guiding channel 322. The annular flange 323 allows an operator to retain the support when sliding the syringe 330 relative to the body 321. The support 320 also comprises a bearing surface 324 against which a rim of the syringe barrel can abut. The bearing surface 324 is substantially flat, has an annular shape and extends in a radial direction relative to the axis of the guiding channel 322. The syringe 330 comprises a syringe barrel 331, a syringe plunger 332, a syringe needle 333 and a needle support 334.

Similarly to apparatus 200, the apparatus 300 comprises releasable connecting means 350. The syringe plunger 332 comprises two fingers 338 extending in two opposite radial directions from the enlarged part 337. The apparatus 300 comprises a spacer 351 having two opposite longitudinal grooves 253, and an elastic open ring 352 prestressed in the hollow body 321 when the apparatus 300 is in a retracted position.

The support 320 comprises a housing 327 for accommodating the elastic ring 352 when the apparatus 300 is brought to the injection position. The support 320 also comprises a lid 328 and a push button 329.

Moreover, in this third embodiment, the syringe barrel 331 comprises a carpule 371 sealed by a protective cap 339. The protective cap 339 protects the composition contained inside the carpule 371.

When the apparatus 300 is in a locked configuration, the syringe barrel 331 and the needle 333 are not connected to each other (the syringe is disassembled). The needle support 334 can slide relative to the body 321 so as to translate the needle 333 relative to the carpule 371. The needle support 334 extends partially outside the body 321, so that it can be operated from outside of the body 321.

The apparatus also comprises a removable safety ring 370 which connects the needle support 334 to the body 321 for preventing movement of the needle support 334 relative to the body 321 when the apparatus is in a locked configuration. The safety ring 370 prevents the cap 339 from being unintentionally pierced by the needle and guarantees that the apparatus 300 has not been previously used.

Figure 16:
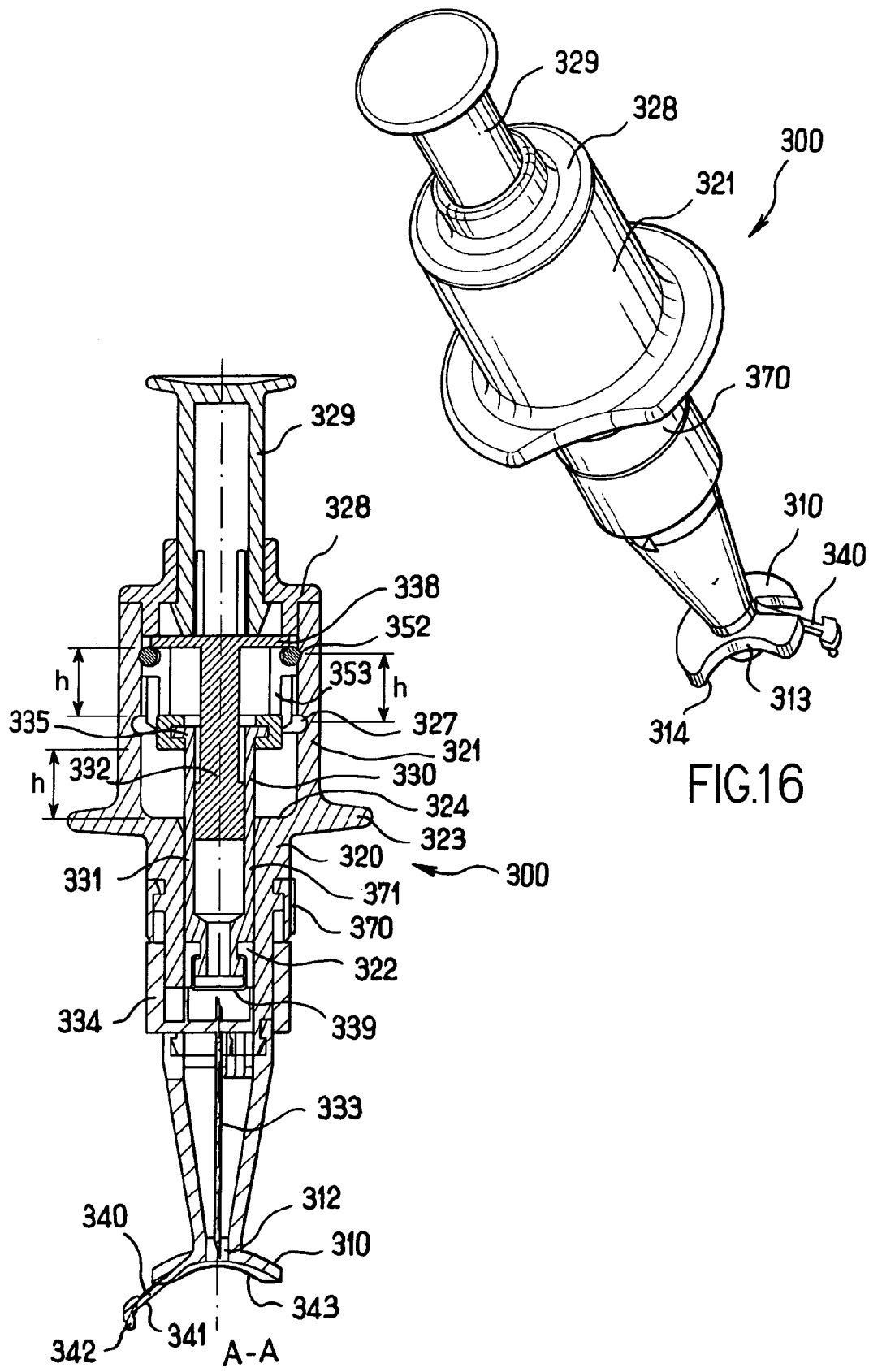
FIG. 16 is a three-dimensional schematic view of an apparatus for intra-ocular injection according to a third embodiment of the invention.
Figure 17:
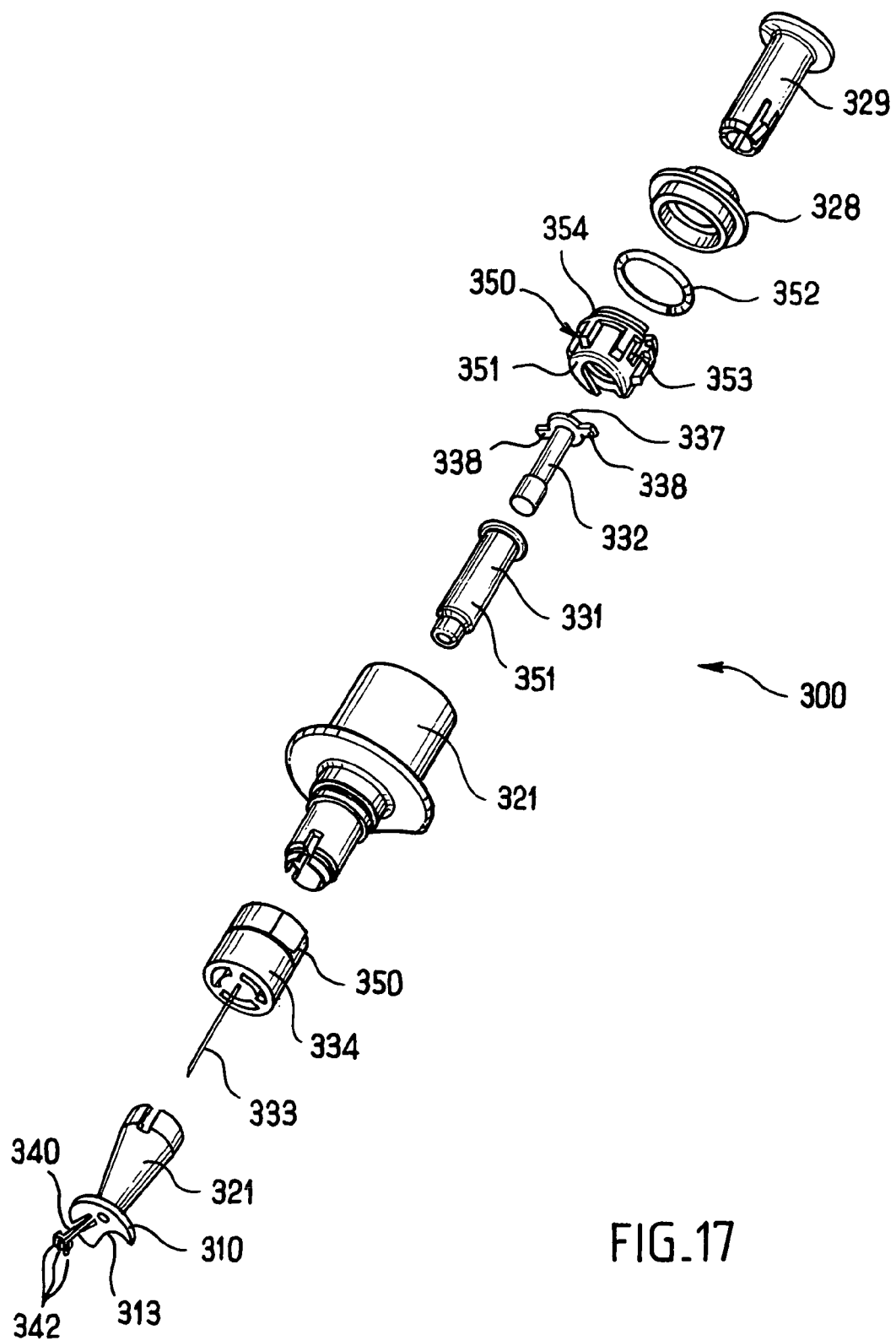
FIG. 17 is an exploded view of the apparatus of FIG. 16.
Figure 19:
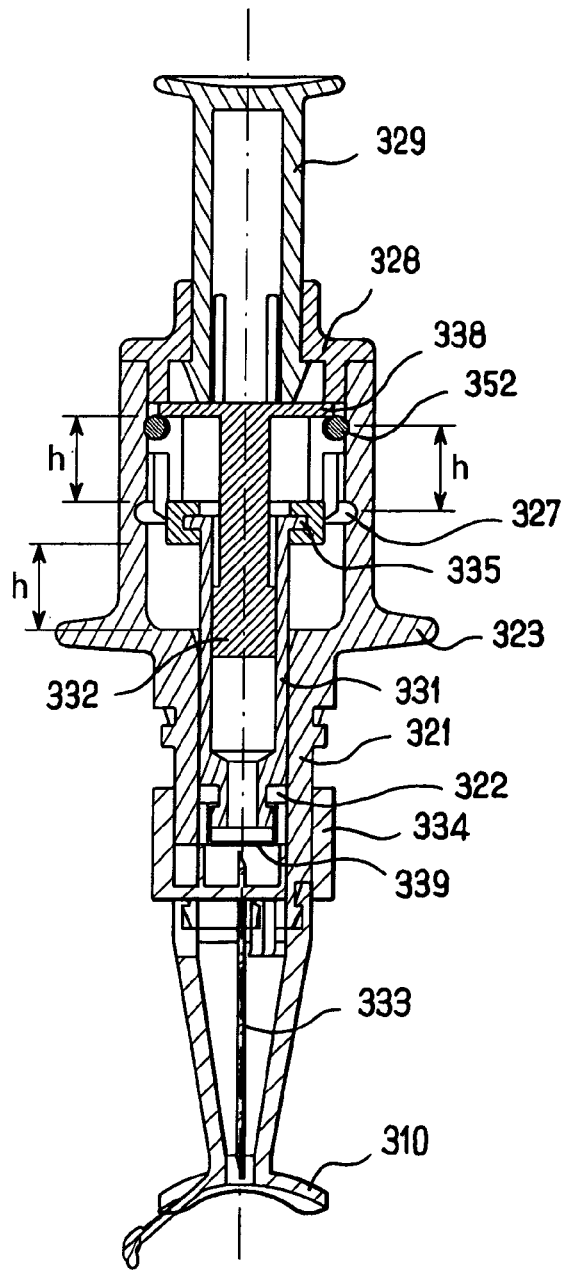
FIGS. 19 to 22 are cut-away views showing the kinematics of the apparatus of FIGS. 16 to 18.
Figure 20:
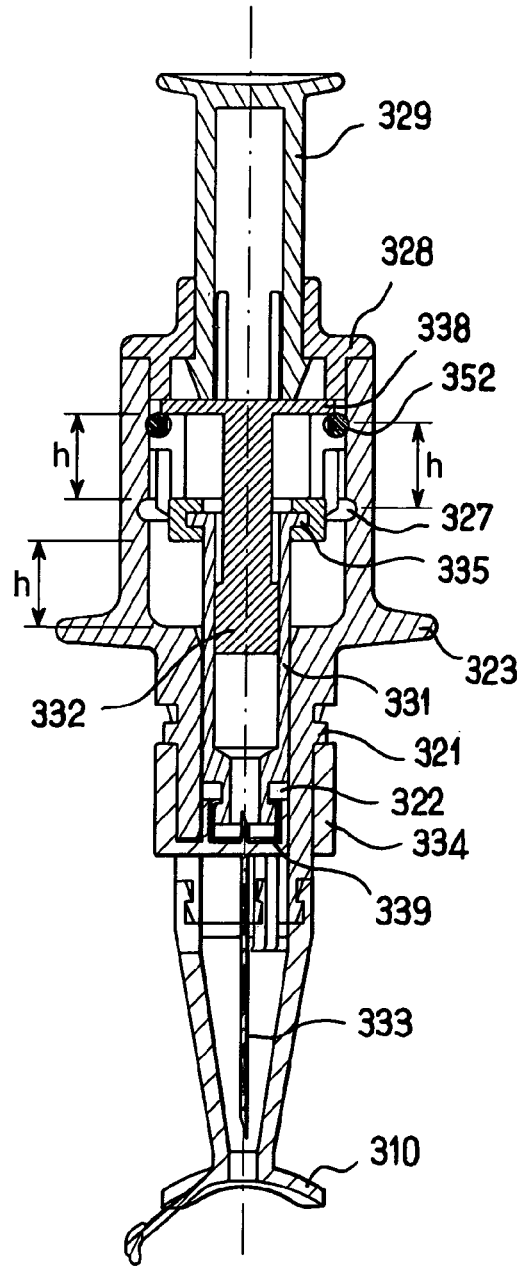
Figures 21, 22:
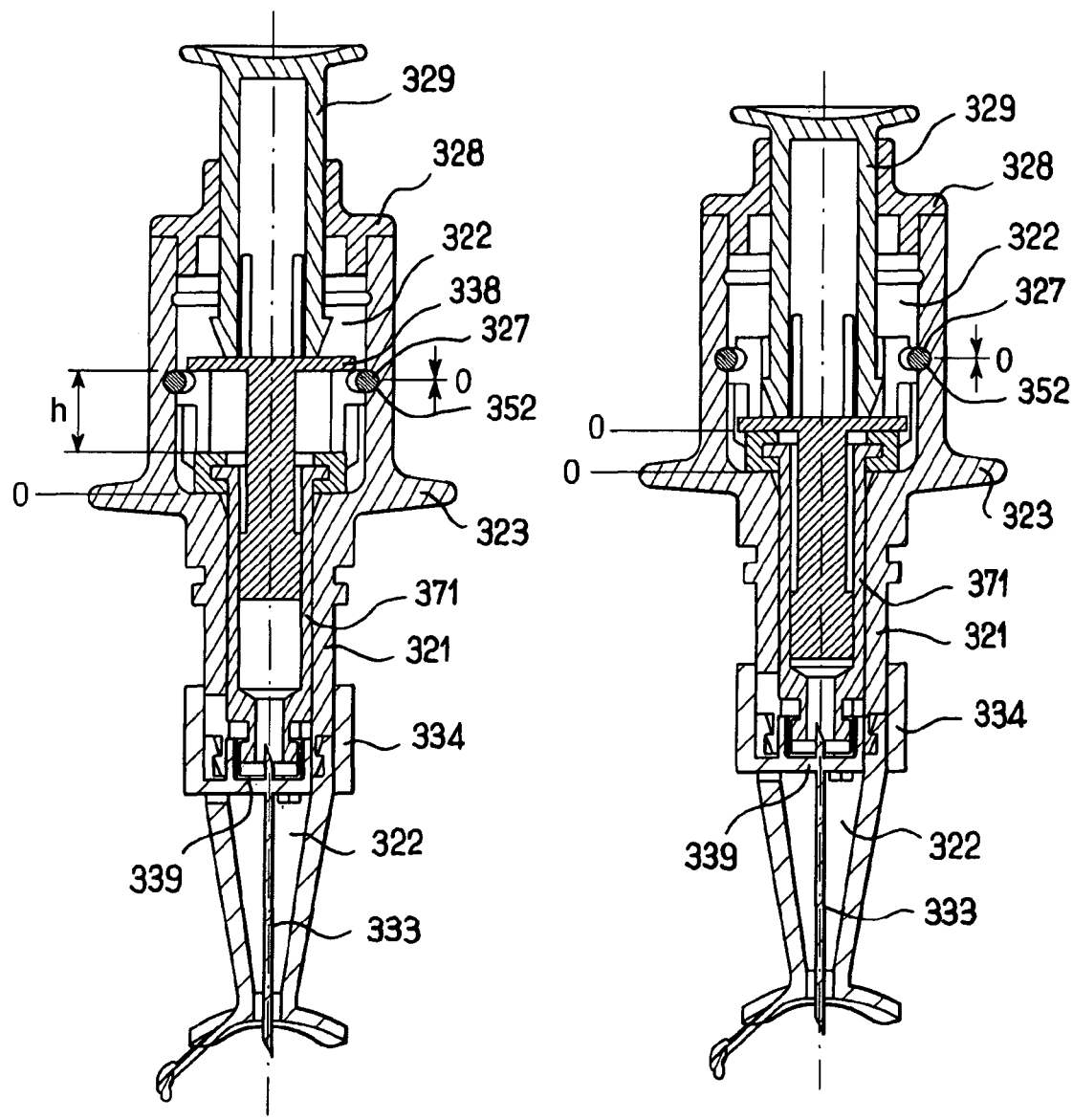

On FIGS. 16 to 18, the apparatus 300 is in a locked configuration wherein the safety ring 370 has not be removed yet and the syringe 330 is represented in a retracted position, the needle 333 extending inside the hollow body 321.

The apparatus 300 is intended to be used in the same way as the apparatus 100 and 200 for performing an intraocular injection (FIGS. 4 to 8), except that it has to be unlocked before use.

FIGS. 19 to 22 illustrate the kinematics of the apparatus 300 when the ophthalmologist removes the safety ring 370 and applies a pressure on the push button 329. According to a first step (FIG. 19), the ophthalmologist unlock the apparatus 300 by removing the safety ring 370. The needle support 334 is thus free to slide relative to the body 321.

According to a second step (FIG. 20), the ophthalmologist takes hold of the needle support 334 and makes it slide relative to the body 321, so as to move the needle 333 relative to the carpule 371 in order to pierce the protective cap 339. During this step, the ophthalmologist simultaneously connects the needle 333 to the barrel 331 to assemble the syringe 330 and pierces the protective cap 339 with the needle 333.

According to a third step (FIGS. 21 and 22), once the syringe has been assembled, the ophthalmologist applies a pressure on the push button 329. Similarly to apparatus 200, in one gesture, by simply exerting a pressure on the push-button 329, the ophthalmologist sequentially causes the syringe 330 to slide towards the injection position (FIG. 21) wherein the needle 333 protrude outside the body 321 and then the plunger 332 to slide relative to the barrel 331 (FIG. 22) in order to inject the composition inside the eye.

Figures 23, 24:
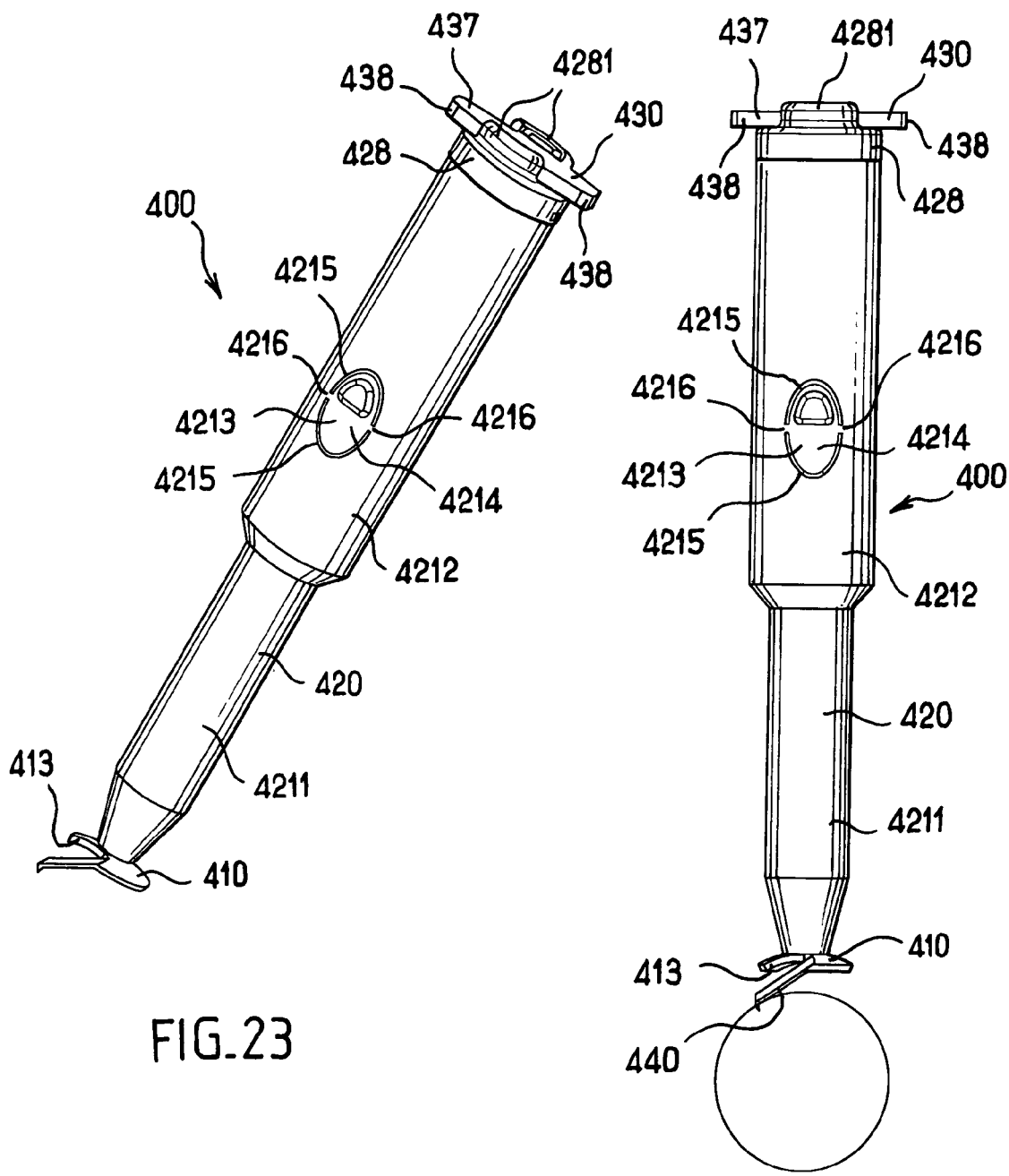
FIGS. 23 and 24 are three-dimensional schematic view of an apparatus for intra-ocular injection according to a fourth embodiment of the invention.
Figure 25:
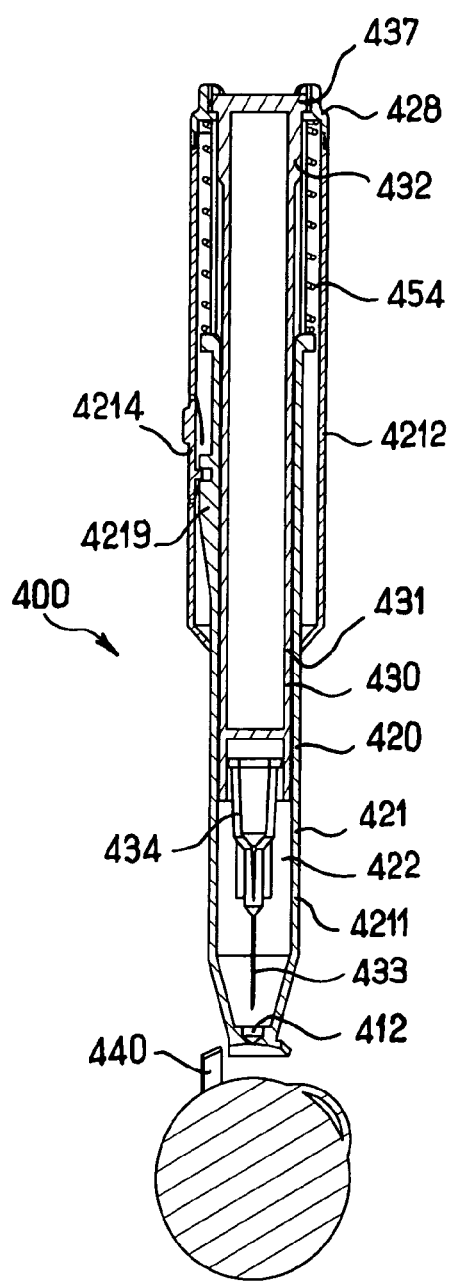
Figure 26:
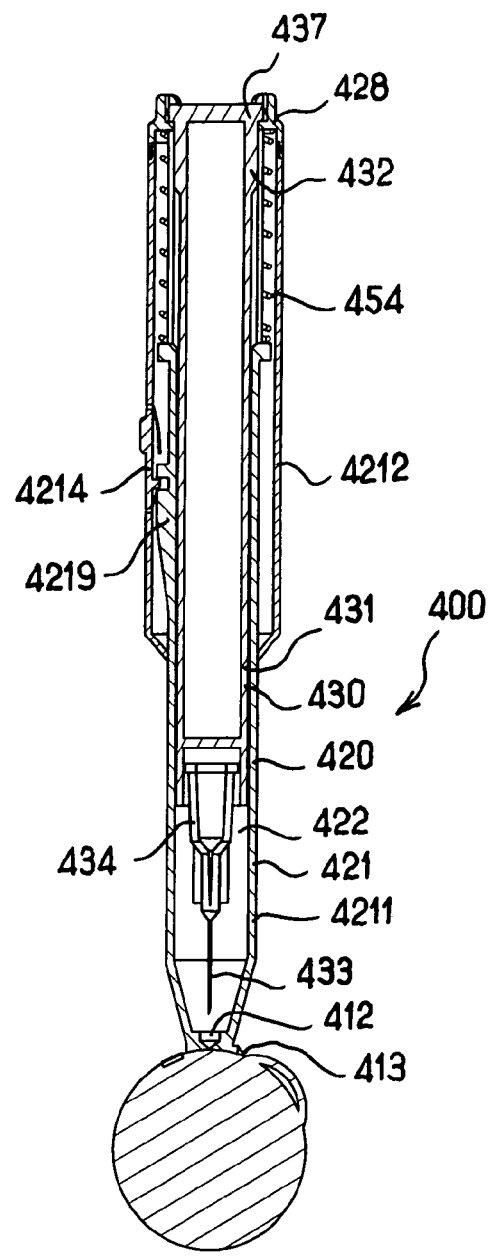
Figure 28:
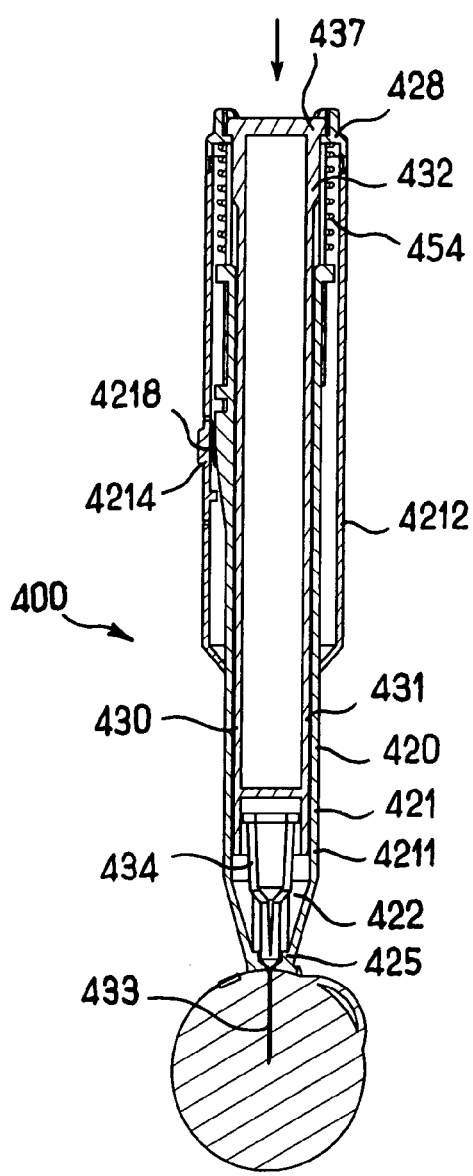
Figure 29:
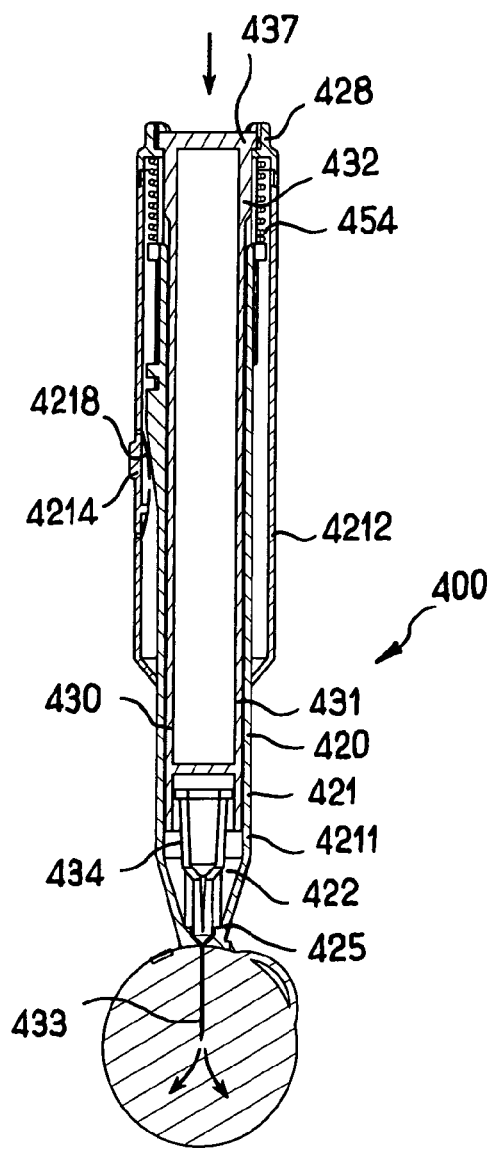

FIGS. 23 and 24 illustrate an apparatus 400 for intra-ocular injection according to a fourth embodiment of the invention. The apparatus 400 comprises a plate 410, a support 420 and a syringe 430. The plate 410 has an eye bearing surface 411, an aperture 412 and a cut-out 413 having an edge 414.

The support 420 comprises a hollow body 421 extending over the aperture 412. According to this fourth embodiment, the hollow body 421 is made of two parts: a first fixed part (or inner part) 4211 which is connected to the plate 410 and a second mobile part (or outer part) 4212 surrounding the inner part 4211. The outer part 4212 is mobile relative to the inner part 4211. More precisely, the outer part 4212 is adapted for sliding along the inner part 4211. The inner part 4211 comprises an inner guiding channel 422 adapted for receiving the syringe 430 in such a way that the syringe 430 can slide into the guiding channel 422. The syringe 430 comprises a syringe barrel 431, a syringe plunger 432, a syringe needle 433 and a needle support 434.

The support 420 also comprises a lid 428 which is fixed at one end of the outer part 4212 of the body 421. The lid 428 closes the end of the outer part 4212 and fixes the syringe barrel 431 to the outer part 4212. To this end, the lid 428 comprises two retaining legs 4281 adapted for holding the enlarged part 437 of the barrel 431 between them.

Moreover, the support 420 comprises a locking member 4213 which prevents movement of the outer part 4212 of the body 421 relative to the inner part 4211 when the apparatus is in a locked configuration. The locking member 4213 thereby prevents that the syringe 430 slides relative to the body 421. The locking member 4213 must be unlocked before use of the apparatus.

On FIGS. 23 to 27, the syringe 430 is represented in a retracted position, in which the needle 433 extends inside the hollow body 421. According to this fourth embodiment, the syringe plunger 432 comprises two fingers 438 extending in two opposite radial directions from the enlarged part 437. According to this fourth embodiment, the apparatus 400 comprises a helical spring 454 arranged between the syringe barrel 431 and the lid 428. The helical spring 454 exerts a force which goes against a sliding movement of the plunger relative to the barrel.

Moreover, according to this fourth embodiment, the locking member 4213 comprises a button 4214. The button 4214 is formed by two curved slots 4215 provided through a wall of the outer part 4212. The slots 4215 delimit a hinge 4216 which allow the button 4214 to be switched. The button 4214 comprises a locking lug 4217 and a friction leg 4218.

The inner part 4211 of the body 421 comprises a bulge 4219 and a groove 4220 for accommodating the locking lug 4217 when the apparatus is in the locked configuration. The groove 4220 is formed at a thickest section of the bulge 4219.

FIGS. 25 to 29 illustrate different steps of a method for performing intra-ocular injection using the apparatus 400. According to a first step (FIG. 25), the ophthalmologist bring the apparatus 400 into contact with an eye. During this step, the resilient member 440 comes first into contact with the eye, causing the superficial layer of the eye to slide over the underlying layer (as already described in connection with FIG. 4).

According to a second step (FIG. 26), the ophthalmologist brings the plate 410 into contact with the superficial layer. The plate 410 is positioned over the eye so that the edge of the cut-out 413 is superimposed on the limbus delimiting the cornea and the sclera of the eye. In such a position of the apparatus, the aperture 412 is situated at a distance of about 3.5 millimeters from the limbus.

According to a third step (FIG. 27), the ophthalmologist unlock the locking member 4213. The ophthalmologist switches the button 4214, thereby removing the lug 4217 from the groove 4220 and bringing the leg 4218 into contact with the inner part 4211 of the body 421. At this stage, the apparatus 400 stands in an unlocked configuration wherein the outer part 4212 can slide relative to the inner part 4212.

According to a fourth step (FIG. 28), the ophthalmologist applies a pressure on the outer part 4212 of the body 421. As a consequence, the outer part 4212 and the syringe 430 are caused to move in a common sliding movement relative to the inner part 4211. The syringe 430 slides into the guiding channel 422 from a retracted position to an injection position in which the needle 433 protrudes out of the body 421 through the aperture 412. During the movement of the syringe, the needle 433 penetrates into the eye until the tip of the needle reaches the vitreous body of the eye.

The leg 4218 rubs against the bulge 4219 of the inner part 4211 of the body 421. The contact between the leg 4218 and the inner part 4211 allows to slow down the movement of the outer part 4212 relative to the inner part 4211 and to avoid abrupt movement therebetween. The bulge 4219 gets thinner along the inner part 4211 in the direction of movement of the leg 4218. The friction leg 4218 and the bulge 4219 allow controlling the sliding movement of the syringe.

During this fourth step, the helical spring 454 prevents a sliding movement of the plunger 432 relative to the barrel 431. The sliding movement of the syringe 430 is finally stopped by the needle support 434 coming into abutment against the bearing surface 425.

According to a fifth step (FIG. 29), the ophthalmologist carries on applying a pressure on the outer part 4212. As a consequence, the helical spring 454 is compressed between the syringe barrel 431 and the lid 428. The plunger 432 slides into the barrel 431, whereby the composition is pushed out of the barrel 431 and injected into the eye via the needle 433.

Similarly to apparatus 200 and 300, in one gesture, by simply exerting a pressure on the outer part 4212, the ophthalmologist sequentially causes the syringe 430 to slide towards the injection position (FIG. 28) wherein the needle 433 protrude outside the body 421 and then the plunger 432 to slide relative to the barrel 431 (FIG. 29) in order to inject the composition inside the eye.

Figures 31, 32:
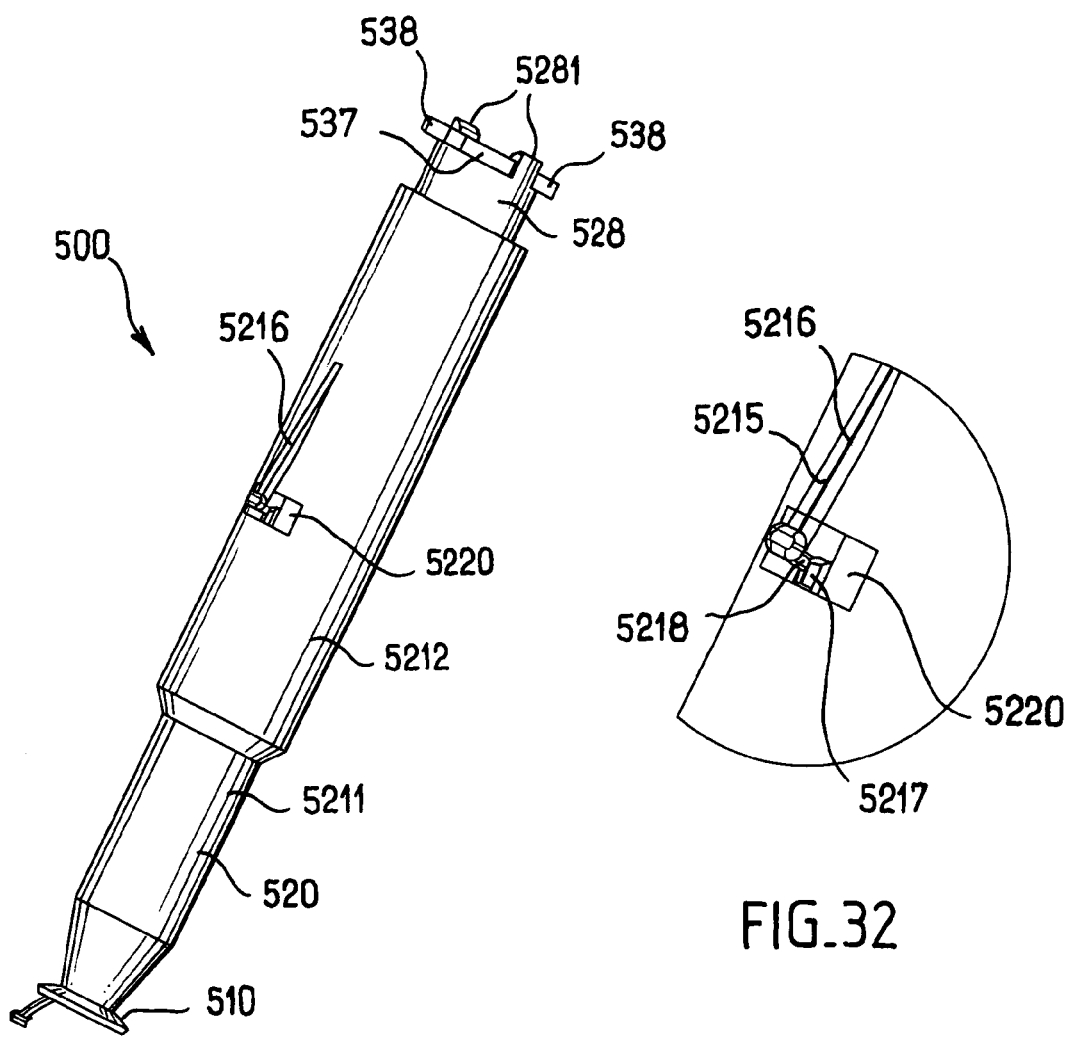
FIG. 31 is a three-dimensional schematic view of an apparatus for intra-ocular injection according to a fifth embodiment of the invention.
FIG. 32 is an enlarged view showing a detail of FIG. 31.
Figures 33, 34:
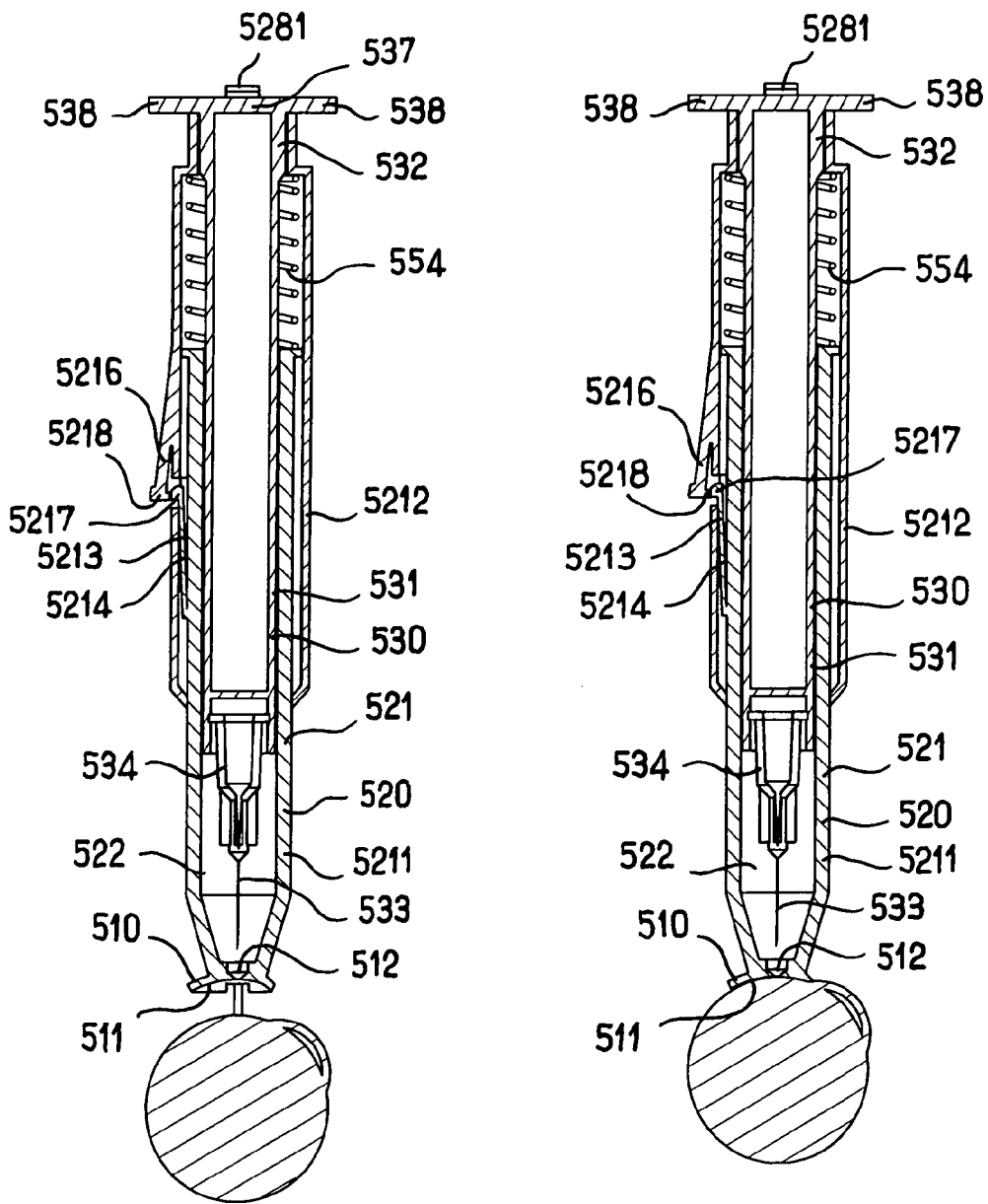
FIGS. 33 to 36 are cut-away views illustrating different steps of a method for performing intra-ocular injection using the apparatus of FIG. 31.
Figure 37:
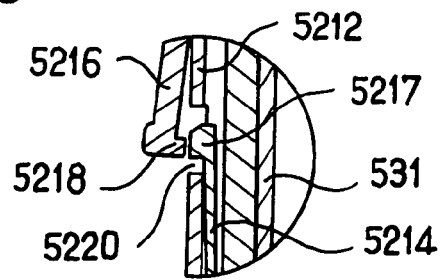
FIG. 37 is an enlarged view showing a detail of FIG. 33.
Figure 35:
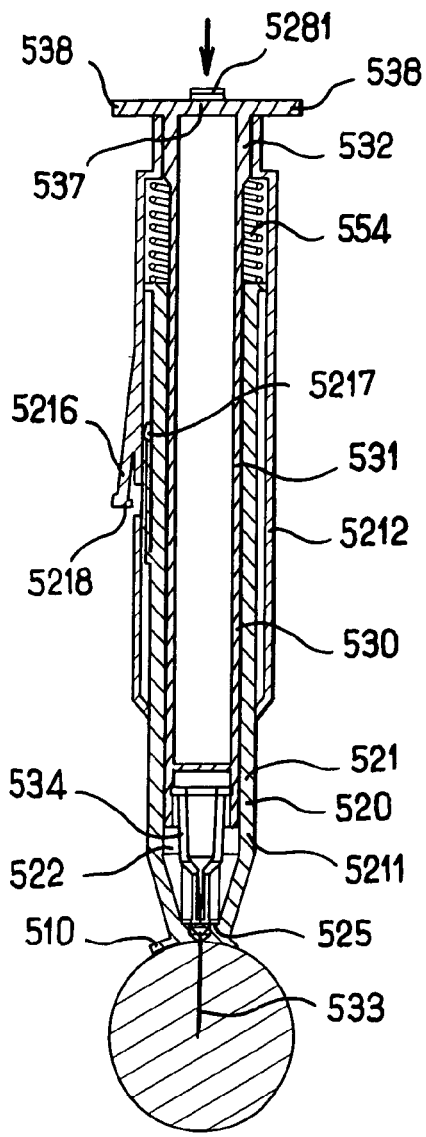

FIGS. 31 and 32 illustrate an apparatus 500 for intra-ocular injection according to a fifth embodiment of the invention. The apparatus 500 comprises a plate 510, a support 520 and a syringe 530. The plate 510 has an eye bearing surface 511, an aperture 512 and a cut-out 513 having an edge 514.

The support 520 comprises a hollow body 521 extending over the aperture 512. The hollow body 521 is made of an inner part 5211 and an outer part 5212 surrounding the inner part 5211, the outer part 5212 being mobile relative to the inner part 5211. The inner part 5211 comprises an inner guiding channel 522 adapted for receiving the syringe 530 in such a way that the syringe 530 can slide into the guiding channel 522. The syringe 530 comprises a syringe barrel 531, a syringe plunger 532, a syringe needle 533 and a needle support 534.

The support 520 also comprises a lid 528 comprising two retaining legs 5281 adapted for holding the enlarged part 537 of the barrel 531 between them. Moreover, the support 520 comprises a locking member 5213 which prevents movement of the outer part 5212 of the body 521 relative to the inner part 5211 when the apparatus is in a locked configuration.

The apparatus 500 is similar to apparatus 400, except that the locking member 5213 comprises a first locking leg 5214 extending from the inner part 5211 of the body 521. The leg 5214 has one end connected to the inner part 5211 and another free end provided with a locking tooth 5217. The outer part 5212 comprises an opening 5220 for accommodating the locking tooth 5217. When the locking tooth 5217 is in the opening 5220, the apparatus 500 is in a locked configuration wherein the locking member 5213 prevents movement of the outer part 5212 of the body 521 relative to the inner part 5211.

The apparatus 500 also comprises an unlocking member 5216 comprising a second unlocking leg 5216 extending from the outer part 5212. The unlocking leg 5216 has one end connected to the outer part 5212 and another free end provided with an unlocking tooth 5218 facing the opening 5220.

The apparatus 500 can be operated in the same way as the apparatus 400 (as illustrated on FIGS. 33 to 36). In order to unlock the apparatus 500, the ophthalmologist pushes the unlocking leg 5216 (FIG. 35), whereby the unlocking tooth 5218 penetrates into the opening 5220 and push the locking tooth 5217 out of the opening 5220 toward the inside of the inner part 5211. As the locking tooth 5217 is removed from the opening 5220, the apparatus 500 is unlocked. The apparatus 500 stands in an unlocked configuration wherein the outer part 5212 can slide along the inner part 5212.

Figure 36:
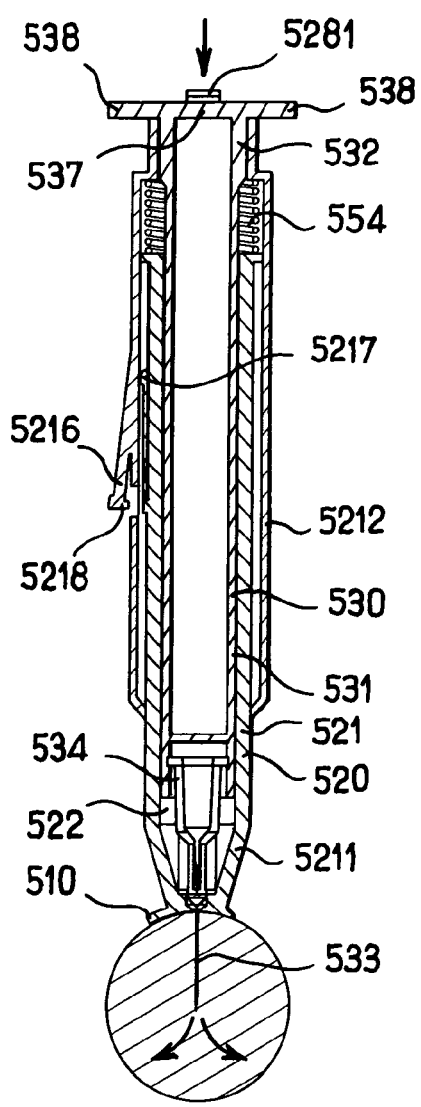

Moreover, during the sliding of the syringe 530 into the guiding channel 522, the locking tooth 5217 rubs against the inner wall of the outer part 5212 of the body 521 (FIG. 36). The contact between the leg 5214 and the outer part 5212 allows to slow down the movement of the outer part 5212 relative to the inner part 5211 and to avoid abrupt movement therebetween. At the same time, the helical spring 554 prevents a sliding movement of the plunger 532 relative to the barrel 531.

FIGS. 38 to 40 illustrate an apparatus 600 for intra-ocular injection according to a sixth embodiment of the invention. The apparatus 600 comprises a plate 610, a support 620 and a syringe 630. The plate 610 has an eye bearing surface 611, an aperture 612 and a cut-out 613 having an edge 614. The support 620 comprises a hollow body 621 extending over the aperture 612. The hollow body 621 is made of an inner part 6211 and an outer part 6212 surrounding the inner part 6211, the outer part being mobile relative to the inner part 6211. The inner part 6211 comprises an inner guiding channel 622 adapted for receiving the syringe 630 in such a way that the syringe 530 can slide into the guiding channel 622. The syringe 630 comprises a syringe barrel 631, a syringe plunger 632, a syringe needle 633 and a needle support 634.

The support 620 also comprises a lid 628 comprising two retaining legs 6281 adapted for holding the enlarged part 637 of the barrel 631 between them. Moreover, the support 620 comprises a locking member 6213 which prevents movement of the outer part 6212 of the body 621 relative to the inner part 6211 when the apparatus is in a locked configuration.

The apparatus 600 is similar to apparatus 400 and 500, except that the locking member 6213 comprises a leg 6214 connected to the outer part 6212 of the body 621 and a locking fork 6215 connected to the leg 6214. The locking fork 6215 has two side branches 6216 extending on both sides of the inner part 6211 of the body 621, each side branch 6216 having a curved end 6217.

Moreover, the inner part 6211 has two grooves 6220 provided on the outer wall of the inner part 6211, for accommodating the ends 6217 of the side branches 6216 when the apparatus is in the locked configuration. The grooves 6220 extends on the inner part 6211 substantially transversally relative to the direction of movement of the outer part 6212.

When the ends 6217 of the side branches 6216 are in the grooves 6220, the apparatus 600 is in a locked configuration wherein the locking member 6213 prevents movement of the outer part 6212 of the body 621 relative to the inner part 6211 (FIGS. 38 to 40).

The apparatus 600 can be operated in the same way as the apparatus 400 and 500 (as illustrated on FIGS. 41 to 44). In order to unlock the apparatus 600, the ophthalmologist pushes the leg 6214 (FIGS. 42 and 46) toward the body 621, whereby the ends 6217 of the locking fork 6215 slide into the grooves 6220 until they get out of the grooves 6220.

When the ends 6217 are removed from the grooves 6220, the apparatus 600 is unlocked. The apparatus 600 stands in an unlocked configuration wherein the outer part 6212 can slide along the inner part 6212. Moreover, during the sliding of the syringe 630 into the guiding channel 622, the helical spring 654 prevents a sliding movement of the plunger 632 relative to the barrel 631 (FIG. 43).

FIGS. 48 to 54 illustrate different steps of a method for performing intra-ocular injection using an apparatus 700 according to a seventh embodiment of the invention. The apparatus 700 comprises a plate 710 adapted for being brought into contact with an eye, a support 720 for receiving a syringe and optionally a syringe 730.

The plate 710 has an eye bearing surface 711 having a curved shape for matingly bearing on the outer surface of the eye and an aperture 712 provided in the plate 710 for allowing a needle to pass through the plate 710.

The support 720 comprises a hollow body 721 extending over the aperture 712. The hollow body 721 is made of two parts: a first part (or inner part) 7211 which is connected to the plate 710 and a second outer part (or outer part) 7212 surrounding the inner part 7211. The outer part 7212 is mobile relative to the inner part 7211. More precisely, the outer part 7212 is adapted for sliding along the inner part 7211. The inner part 7211 comprises an inner guiding channel 722 adapted for receiving the syringe 730 in such a way that the syringe 730 can slide into the guiding channel 722.

According to this seventh embodiment, the apparatus 700 comprises a helical spring 754 arranged between the inner part 7211 and the outer part 7212 of the body 721. The helical spring 754 exerts a force which goes against a sliding movement of the outer part 7212 relative to the inner part 7211.

The syringe 730 comprises a syringe barrel 731, a syringe plunger 732, a syringe needle 733 and a needle support 734 for securing the needle to the barrel 731. The plunger 732 has an enlarged part 737 which is used by an ophthalmologist to apply a pressure on the plunger 732 in order to make it slide into the barrel 731. The apparatus 700 also comprises a resilient member 740, the resilient member 740 comprising a flexible leg 741.

FIGS. 48 to 54 illustrate different steps of a method for performing intra-ocular injection using the apparatus 700. According to a first step (FIG. 48), the syringe 730 is filled with a compound or composition of interest (i.e. the therapeutic medium).

According to a second step (FIG. 49), the syringe 730 is inserted in the inner guiding channel 722 and the syringe barrel 731 is locked to the outer part 7212 of the body 721.

According to a third step (FIG. 50), the apparatus 700 is brought into contact with an eye. During this step, the resilient member 740 comes first into contact with the eye. The flexible leg 741 engages a superficial layer 1 of the eye extending over an underlying layer 2. While the flexible leg 741 is urged against the superficial layer 1, the superficial layer 1 is caused to slide over the underlying layer 2.

According to a fourth step (FIG. 51), when the plate 710 is in contact with the eye, the ophthalmologist applies a pressure on the syringe plunger 732. As a consequence, the syringe 730 slides into the guiding channel 722 from a retracted position to an injection position in which the needle 733 protrudes out of the body 721 through the aperture 712. During the movement of the syringe, the needle 733 penetrates into the eye through the different layers 1, 2 of the eye until the tip of the needle reaches the vitreous body of the eye.

The outer part 7212 follows the movement of the syringe 730. As the outer part 7212 of the body 721 slides relative to the inner part 7211 of the body 721, the helical spring 754 is stretched, thereby exerting an increasing restoring force on the outer part 7212. When the restoring force exerted by the helical spring 754 become greater than the force necessary for pushing the syringe plunger 732 into the syringe barrel 731, the sliding movement of the outer part 7212 is stopped and the syringe plunger 732 starts sliding into the syringe barrel 731. The characteristics of the helical spring 754 are chosen such that the stroke of the syringe is L, in order that the needle 733 penetrates into the eye at a depth of about 3 to about 10 millimeters (e.g. 6 millimeters).

According to a fifth step (FIG. 52), the ophthalmologist carry on applying a pressure on the plunger 732. As a consequence, the plunger 732 slides into the barrel 731, whereby the composition is pushed out of the barrel 731 and injected into the eye via the needle 733.

The fourth and fifth steps are performed successively while the ophthalmologist is continuously applying a pressure on the plunger 732. This is due to the fact that the force required for moving the syringe 730 relative to the body 721 is initially lower than the force required for moving the plunger 732 relative to the barrel 731.

According to a sixth step (FIG. 53), once the ophthalmologist has performed the injection, the ophthalmologist stops applying a pressure on the plunger 732. As a consequence, the helical spring 754 returns back to its initial shape, which causes the outer part 7212 of the body 721 to slide relative to the inner part 7211 back to its initial position. As the syringe 730 follows the movement of the outer part 7212 of the body 721, the needle 733 is retracted inside the body 721.

According to a seventh step, the apparatus 700 is removed from the eye. Thus the resilient member 740 is moved away from the eye. As a consequence, the superficial layer 1 slides over the underlying layer 2, back to its initial position.

FIGS. 55 to 58 are schematic cut-away views of variants 700', 700'', 700''' and 700'''' of the seventh embodiment. On FIG. 55, the body 721 comprises a first part 7211' and a second part 7212'. According to this variant, the first part 7211' is an outer part whereas the second part 7212' is an inner part which is mobile relative to an outer part. The apparatus 700' comprises a helical spring 754 which is arranged between the inner part 7211' and the outer part 7212' of the body 721. According to this variant, the helical spring 754 is compressed when a pressure is applied on the plunger 732.

Figures 55, 56, 57, 58:
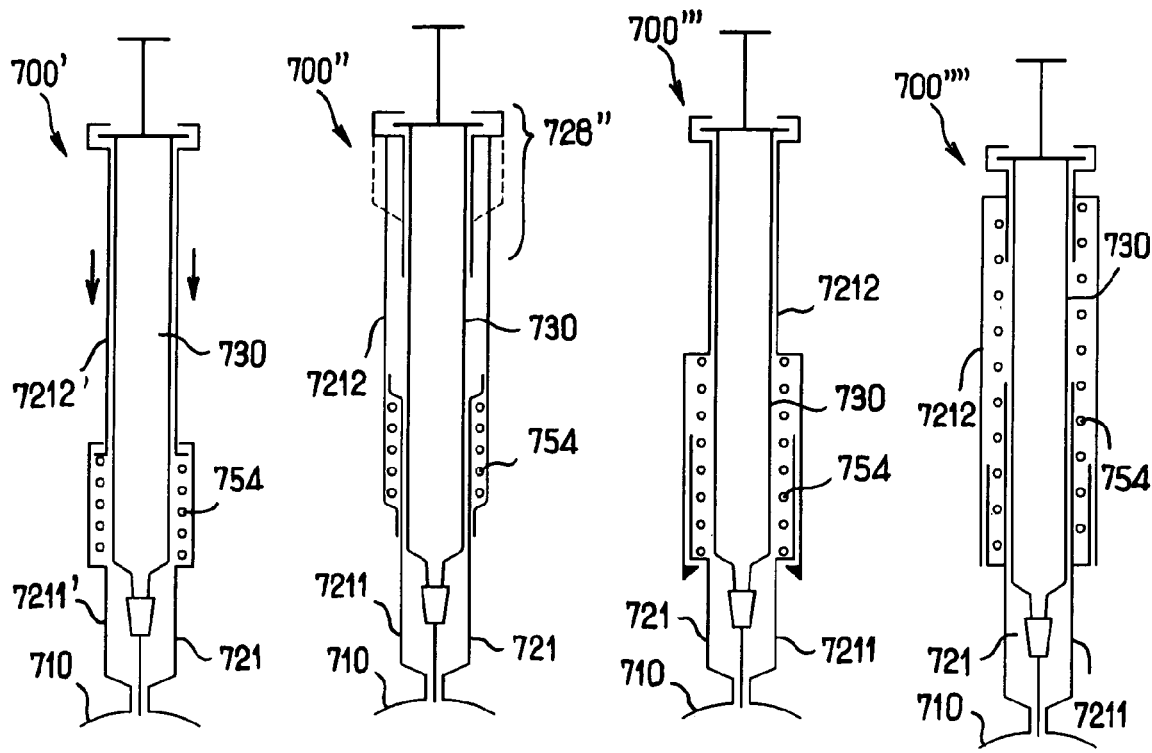
FIGS. 55 to 58 are schematic cut-away views of variants of the seventh embodiment.

On FIG. 56, the apparatus 700'' further comprises an adaptor 728'' so that the apparatus can accommodate different types of syringes (with different diameters and/or lengths).

On FIG. 57, the apparatus 700''' comprises a helical spring 754 which is arranged between the inner part 7211 and the outer part 7212 of the body 721. According to this variant, the helical spring 754 is compressed when a pressure is applied on the plunger 732.

Figures 59, 60:
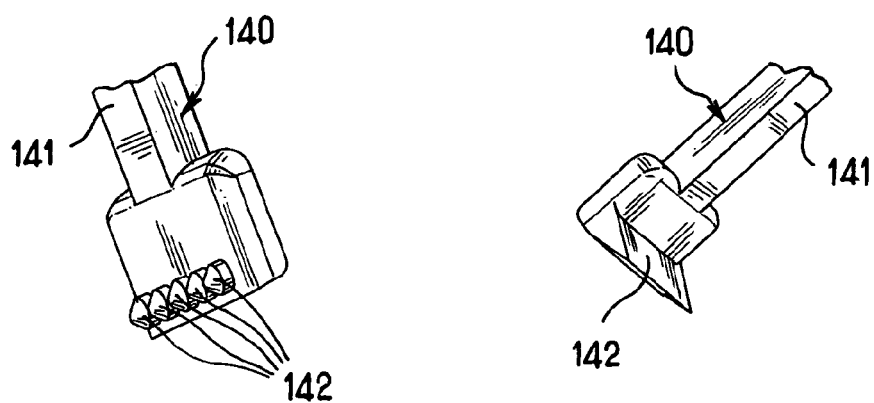
FIGS. 59 and 60 are schematic views of possible forms of flexible legs which can be used in the apparatus represented on FIGS. 1 to 58.

FIGS. 59 and 60 are schematic views of possible forms of flexible legs which can be used in the apparatus represented on FIGS. 1 to 58. On FIG. 59, the resilient member 140 comprises a flexible leg 141 and a plurality of teeth 142 (or pins) arranged at the free end of the flexible leg 141. Thereby the resilient member has a general shape of a "comb" or a "rake".

Alternatively, as shown on FIG. 60, the resilient member 140 can comprise a flexible leg 141 and a unique elongated tooth 142 (or rib). Thereby the resilient member has a general shape of a "scraper".

According to particular embodiment, the syringe of the invention is containing a therapeutic medium and thus forms a reservoir of the therapeutic medium. In this way, the therapeutic delivery apparatus of the present invention provides a mechanism for intraocular administration or delivery of a therapeutic medium to a posterior segment of a mammalian eye, more particularly a human eye as well as a methodology for treating and/or preventing disorders and/or diseases of the eye, in particular retinal/choroidal disorders or diseases, through such intraocular administration of such therapeutic mediums. Such methodologies provide a mechanism for treating a wide array of diseases and/or disorders of an eye of a mammal, more specifically a human eye, and more particularly diseases or disorders involving the posterior segment of the eye such as retinal/choroidal disorders or diseases. Such a treatment/prevention methodology also is useable to treat/prevent a number of vision-threatening disorders or diseases of the eye of a mammal including, but not limited to diseases of the retina, retinal pigment epithelium (RPE) and choroid. Such vision threatening diseases include, for example, ocular neovascularization, ocular inflammation and retinal degenerations. Specific examples of these disease states include diabetic retinopathy, chronic glaucoma, retinal detachment, sickle cell retinopathy, age-related macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, and retinal artery occlusion, and, neovascularization due to penetration of the eye or ocular injury. The methodology of the present invention also can be used to treat ocular symptoms resulting from diseases or conditions that have both ocular and non-ocular symptoms.

As used in the present invention, therapeutic medium includes any compound, agent or the like known in the art that when administered or delivered intraocularly (and more specifically intravitreously), is effective in obtaining a desired local or systemic physiological or pharmacological effect. More particularly, in the present invention, therapeutic medium includes, but is not limited to drugs, medicaments, antibiotics, antibacterials, antiproliferatives, neuroprotectives, anti-inflammatories (steroidal and non-steroidal), growth factors, neurotropic factors, antiangiogenics, thrombolytics or genes. Exemplary therapeutic mediums include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1-3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like or combination thereof.

Antiproliferatives include any of a number of compounds, agents, therapeutic mediums or drugs known to those skilled in the art that inhibit the proliferation of cells. Such compounds, agents, therapeutic mediums or drugs include, but are not limited to, 5-fluorouracil, taxol, rapamycin, mitomycin C and cisplatin.

Neuroprotectives include any of a number of compounds, agents, therapeutic mediums or drugs known to those skilled in the art that guard or protect against neurotoxicity; the quality of exerting a destructive or poisonous effect upon nerve tissue. Such compounds, agents, therapeutic mediums or drugs include, but are not limited to, lubezole.

Anti-inflammatories include any of a number of compounds, agents, therapeutic mediums or drugs known to those skilled in the art, either steroidal or non-steroidal, and generally characterized has having the property of counteracting or suppressing the inflammatory process. Non-steroidal inflammatory drugs or compounds comprise a class of drugs which shares the property of being analgesic, antipyretic and anti-inflammatory by way of interfering with the synthesis of prostaglandins. Such non-steroidal anti-inflammatories include, but are not limited to, indomethacin, ibuprofen, naxopren, piroxicam and nabumetone.

Such anti-inflammatory compounds contemplated for use in the methodology of the present invention, include those described in U.S. Pat. No. 6,955,815, U.S. Pat. No. 6,897,206, U.S. Pat. No. 6,846,816 or U.S. Pat. No. 6,693,125 the teachings of which are incorporated herein by reference. In an exemplary embodiment, an anti-inflammatory steroid contemplated for use in the methodology of the present invention is triamcinolone acetonide, prednisolone and the like. Corticosteroids contemplated for use in the methodology of the present invention include, for example, triamcinolone, dexamethasone, fluocinolone, cortisone, prednisolone, flumetholone, and derivatives thereof (see also U.S. Pat. No. 5,770,589).

Other anti-inflammatories or anti-inflammatory factors contemplated for use in the present invention include antiflammins (e.g. U.S. Pat. No. 5,266,562), beta-interferon (IFN-beta), alpha-interferon (IFN-alpha), TGF-beta, interleukin-10 (XL-10), cyclosporines (e.g. cyclosporine A) and glucocorticoids and mineralocorticoids from adrenal cortical cells. It should be noted that certain biologically active materials can have more than one activity. For example, it is believed that IFN-alpha and IFN-beta have activities as both anti-inflammatory molecules and as anti-angiogenic molecules. In exemplary embodiments, the dosage of anti-inflammatory factors being delivered to the sub-retinal space is contemplated as being in a dosage range of 50 pg to 500 ng, preferably 100 pg to 100 ng, and most preferably 1 ng to 50 ng per eye per patient per day.

As is known to those skilled in the art, growth factors is a collective term originally used to refer to substances that promote cell growth and is now loosely used to describe molecules that function as growth stimulators (mitogens) but also as growth inhibitors (sometimes referred to as negative growth factors), factors that stimulate cell migration, or as chemotactic agents or inhibit cell migration or invasion of tumor cells, factors that modulate differentiated functions of cells, factors involved in apoptosis, factors involved in angiogenesis, or factors that promote survival of cells without influencing growth and differentiation. In the present invention, such growth factors include, but are not limited to, pigment epithelium derived factor and basic fibroblast growth factor.

As is known to those skilled in the art, neurotropic factors is a general term used to describe growth factors and cytokines that can enhance neuronal survival and axonal growth and that regulate synaptic development and plasticity in the nervous system. In the present invention, such growth factors include, but are not limited to, ciliary neurotrophic factors and brain-derived neurotrophic factors.

Antiangiogenics include any of a number of compounds, agents, therapeutic mediums or drugs known to those skilled in the art that inhibit the growth and production of blood vessels, including capillaries. Such compounds, agents, therapeutic mediums or drugs include, but are not limited to, anecortave acetate and anti VEGF antibody. Other antiangiogentics or anti-angiogenic factors contemplated for use with the methodology of the present invention include vasculostatin, angiostatin, endostatin, anti-integrins, vascular endothelial growth factor inhibitors (VEGF-inhibitors), platelet factor 4, heparinase, and bFGF-binding molecules. The VEGF receptors Flt and Flk are also contemplated. When delivered in the soluble form these molecules compete with the VEGF receptors on vascular endothelial cells to inhibit endothelial cell growth. VEGF inhibitors may include VEGF-neutralizing chimeric proteins such as soluble VEGF receptors. In particular, they may be VEGF-receptor-IgG chimeric proteins. Another VEGF inhibitor contemplated for use in the present invention is antisense phosphorothiotac oligodeoxynucleotides (PS-ODNs). In exemplary embodiments, the dosage of anti-angiogenic factors being delivered to the sub-retinal space is contemplated as being in a dosage range of 50 pg to 500 ng, preferably 100 pg to 100 ng, and most preferably 1 ng to 50 ng per eye per patient per day.

Thrombolytics, as is known to those skilled in the art include any of a number of compounds, agents, therapeutic mediums or drugs that dissolve blot clots, or dissolve or split up a thrombus. Such thrombolytics include, but are not limited to, streptokinase, tissue plasminogen activator or TPA and urokinase.

Other factors contemplated for use in the present invention for retarding cell degeneration, promoting cell sparing, or promoting new cell growth include neurotrophin 4/5 (NT4/5), cardiotrophin-1 (CT-1), ciliary neurotrophic-factor (CNTF), glial cell line derived neurotrophic factor (GDNF), nerve growth factor (NGF), insulin-like growth factor-1 (IGF-1), neurotrophin 3 (NT-3), brain-derived neurotrophic factor (BDNF), PDGF, neurturin, acidic fibroblast growth factor (aFGF), basic fibroblast growth factor (bFGF), EGF, neuregulins, heregulins, TGF-alpha, bone morphogenic proteins (BMP-1, BMP-2, BMP-7, etc.), the hedgehog family (sonic hedgehog, Indian hedgehog, and desert hedgehog, etc.), the family of transforming growth factors (including, e.g., TGF.beta.-1, TGF.beta.-2, and TGF.beta.-3), interleukin 1-B (IL1-.beta.), and such cytokines as interleukin-6 (EL-6), IL-10, CDF/LIF, and beta-interferon (IFN-.beta.). In exemplary embodiments, the dosage of such factors being delivered to the sub-retinal space is contemplated as being in a dosage range of 50 pg to 500 ng, preferably 100 pg to 100 ng, and most preferably 1 ng to 50 ng per eye per patient per day.

The therapeutic medium delivery apparatus and methodology of the present invention advantageously delivers the therapeutic medium to the target or disease site and thus the eye as compared to current systemic and intraocular routes of administration. More particularly, the delivery apparatus and methodology of the present invention limit corneal injury and/or therapeutic medium leakage after injection.

It is understood that the amount of the therapeutic medium that is to be delivered to the treatment site is readily calculable by one of ordinary skill in the art without undue experimentation and will vary depending on the disease or disorder to be treated and the particular treatment circumstances. In addition, the amount also will depend upon the particular formulation of the therapeutic medium. Further, the amount of the therapeutic medium to be delivered also takes into account the period of time expected for administration and/or treatment and/or the frequency or periodicity of such administration and/or treatment. The formulation also ordinarily takes into account pH, osmolarity and toxicity. In more particular embodiments, the therapeutic medium is in the form of one of a solution, a composition or a liquid.

The therapeutic medium also can include a pharmaceutically acceptable carrier or excipient and/or one or more accessory molecules which may be suitable for diagnostic or therapeutic use in vitro or in vivo. The term "pharmaceutically acceptable carrier" as used herein encompasses any of the standard pharmaceutical carriers, such as a phosphate buffered saline solution, water, and emulsions, such as an oil/water or water/oil emulsion, and various types of wetting agents. The therapeutic medium also can include stabilizers and preservatives. For examples of carriers, stabilizers and adjuvants, see Martin Remington's Pharm. Sci., 15th Ed. (Mack Publ. Co., Easton (1975)).

It also should be recognized, that the therapeutic medium delivery apparatus and methodologies of the present invention are contemplated as being practiced alone, or in combination with other therapies or treatments. (for example in combination with laser treatment) before and/or after said treatment. In addition, it is contemplated that the therapeutic medium can comprise a mixture of active agents or therapeutic agents such as for example antibiotics, medicaments, or agents, e.g., thalidomide, being administered along with a steroid.

Most, if not all, ophthalmic diseases and disorders are associated with one or more of three types of indications: (1) angiogenesis, (2) inflammation, and (3) degeneration. Based on the indications of a particular disorder, one of ordinary skill in the art can administer any suitable therapeutic medium molecule from the three groups at a therapeutic dosage. The following describes some ophthalmic diseases and disorders and a form of treatment therefore. It should be recognized however, that the following is by way of illustration and is not intended to limit usage of the therapeutic medium delivery apparatus or methodologies of the present invention to a particular technique or therapeutic medium for treatment of an eye disease or disorder.

Diabetic retinopathy for example, is characterized by angiogenesis. This invention contemplates treating diabetic retinopathy by delivering one or more anti-angiogenic factors into the intraocular space. It also is desirable to co-deliver one or more neurotrophic factors.

Uveitis involves inflammation. The present invention contemplates treating uveitis by instilling or disposing one or more anti-inflammatory factors in the intraocular space.

Retinitis pigmentosa, by comparison, is characterized by retinal degeneration. The present invention contemplates treating retinitis pigmentosa by instilling or disposing one or more neurotrophic factors in the intraocular space.

Age-related macular degeneration involves both angiogenesis and retinal degeneration and includes, but is not limited to, dry age-related macular degeneration, exudative age-related macular degeneration, and myopic degeneration. The present invention contemplates treating this disorder by instilling or disposing in the intraocular space one or more neurotrophic factors and/or one or more anti-angiogenic. More particularly, the methodology contemplates instilling or disposing a corticosteriod in the intraocular space.

Glaucoma is characterized by increased ocular pressure and loss of retinal ganglion cells. Treatments for glaucoma contemplated in the present invention include delivery of one or more neuroprotective agents that protect cells from excitotoxic damage. Such agents include N-methyl-D-aspartate (NMDA) antagonists, cytokines, and neurotrophic factors.

As noted above, administration of the therapeutic medium is not limited to those uses involving the diagnosed existence of a disorder or disease. It is contemplated that the therapeutic medium delivery apparatus can be used for prophylactic administration of the therapeutic medium. For example, in more than 50% of cases where AMD occurs in one eye, it will subsequently occur in the unaffected eye within a year. In such cases, prophylactic administration of a therapeutic medium such as a steroid into the unaffected eye may prove to be useful in minimizing the risk of, or preventing, AMI in the unaffected eye.

All patents, published patent applications and other references disclosed herein are hereby expressly incorporated by reference in their entireties by reference.

Those skilled in the art will recognize, or be able to ascertain using no more than routine experimentation, many equivalents of the specific embodiments of the invention described herein. Such equivalents are intended to be encompassed by the following claims.

NUMERAL REFERENCES 1 superficial layer
2 underlying layer
100 apparatus for intra-ocular injection
110 plate
111 eye bearing surface
112 aperture
113 cut-out
114 edge
120 support
121 hollow body
122 guiding channel
123 annular flange
124 first bearing surface
125 second bearing surface
130 syringe
131 syringe barrel
132 syringe plunger
133 syringe needle
134 needle support
135 annular rim
136 annular rim
137 enlarged part
140 resilient member
141 flexible leg
142 teeth
200 apparatus for intra-ocular injection
210 plate
211 eye bearing surface
212 aperture
213 cut-out
214 edge
220 support
221 hollow body
222 guiding channel
223 annular flange
224 bearing surface
227 housing
228 lid
229 push button
230 syringe
231 syringe barrel
232 syringe plunger
233 syringe needle
234 needle support
235 annular rim
236 annular rim
237 enlarged part
238 fingers
240 resilient member
241 flexible leg
242 teeth
250 releasable connecting means
251 spacer
252 elastic open ring
253 longitudinal grooves
260 removable cap
300 apparatus for intra-ocular injection
310 plate
311 eye bearing surface
312 aperture
313 cut-out
314 edge
320 support
321 hollow body
322 guiding channel
323 annular flange
324 bearing surface
327 housing
328 lid
329 push button
330 syringe
331 syringe barrel
332 syringe plunger
333 syringe needle
334 needle support
335 annular rim
336 annular rim
337 enlarged part
338 fingers 339 protective cap
340 resilient member
341 flexible leg
342 teeth
350 releasable connecting means
351 spacer
352 elastic open ring
353 longitudinal grooves
370 removable safety ring
371 carpule
400 apparatus for intra-ocular injection
410 plate
411 eye bearing surface
412 aperture
413 cut-out
414 edge
420 support
421 hollow body
4211 inner part
4212 outer part
4213 locking member
4214 button
4215 slots
4216 hinge
4217 locking lug
4218 friction leg
4219 bulge
4220 groove
422 guiding channel
425 bearing surface
428 lid
4281 Retaining legs
430 syringe
431 syringe barrel
432 syringe plunger
433 syringe needle
434 needle support
435 annular rim
437 enlarged part
438 fingers
441 flexible leg
442 teeth
454 helical spring
500 apparatus for intra-ocular injection
510 plate
511 eye bearing surface
512 aperture
513 cut-out
514 edge
520 support
521 hollow body
5211 inner part
5212 outer part
5213 locking member
5214 locking leg
5215 unlocking member
5216 unlocking leg
5217 locking tooth
5218 unlocking tooth
5220 opening
522 guiding channel
525 bearing surface
528 lid
5281 retaining legs
530 syringe
531 syringe barrel
532 syringe plunger
533 syringe needle
534 needle support
535 annular rim
537 enlarged part
538 fingers
541 flexible leg
542 teeth
554 helical spring
600 apparatus for intra-ocular injection
610 plate
611 eye bearing surface
612 aperture
613 cut-out
614 edge
620 support
621 hollow body
6211 inner part
6212 outer part
6213 locking member
6214 leg
6215 locking fork
6216 side branches
6217 ends
6220 grooves
622 guiding channel
625 bearing surface
628 lid
6281 retaining legs
630 syringe
631 syringe barrel
632 syringe plunger
633 syringe needle
634 needle support
635 annular rim
637 enlarged part
638 fingers
641 flexible leg
642 teeth
654 helical spring
700 apparatus for intra-ocular injection
710 plate
711 bearing surface
712 aperture
720 support
721 hollow body
7211 inner part
7212 outer part
722 guiding channel
730 syringe
731 syringe barrel
732 syringe plunger
733 syringe needle
734 needle support
737 enlarged part
740 resilient member
741 flexible leg
754 helical spring
700' apparatus for intra-ocular injection
7211' outer part
7212' inner part
700" apparatus for intra-ocular injection
728" adaptor
700'" apparatus for intra-ocular injection
700"" apparatus for intra-ocular injection

The invention claimed is:

1. An apparatus for intraocular injection comprising a plate adapted for being brought into contact with an eye, a guide operable to guide a needle into the interior of an eye, and a member operable to displace a superficial layer of the eye over an underlying layer of the eye as the plate is brought into contact with the eye before the needle is guided into the interior of the eye.

2. The apparatus according to claim 1, wherein the member operable to displace a superficial layer over an underlying layer is a resilient member which can be bent when urged against the superficial layer, whereby the resilient member applies a tangential force to the superficial layer.

3. The apparatus according to claim 2, wherein the resilient member comprises a flexible leg protruding from the plate.

4. The apparatus according to claim 2, wherein the member operable to displace a superficial layer over an underlying layer comprises at least one tooth adapted to engage the superficial layer.

5. The apparatus according to claim 4, wherein the means for engaging the superficial layer comprises a plurality of teeth.

6. The apparatus according to claim 4, wherein the tooth is provided at a free end of the flexible leg.

7. The apparatus according to claim 1, wherein the plate comprises a cut-out having an edge adapted to be positioned along the limbus delimiting the cornea and the sclera of the eye, so as to adjust the position of the guiding means with respect to the limbus.

8. The apparatus according to claim 7, wherein the edge of the cut-out is of substantially circular shape.

9. The apparatus according to claim 7, wherein the edge of the cut-out has a shape which corresponds to a shape of a limbus so that the edge can be superimposed on the limbus.

10. The apparatus according to claim 9, wherein the cutout is arranged in the plate such that when the edge of the cut-out is superposed on the limbus, the plate extends over the sclera of the eye.

11. The apparatus according to claim 7, wherein the cut-out and the guide are arranged so that the needle penetrates into the eye through the sclera at a distance of about 3.5 millimeters from the limbus.

12. The apparatus according to claim 1, wherein the plate has an eye bearing surface having a curved shape for matingly bearing on the outer surface of the eye.

13. The apparatus according to claim 1, wherein the guide comprises a support having a hollow body adapted for receiving a barrel of a syringe, such that the syringe can slide relative to the body.

14. The apparatus according to claim 13, wherein the syringe is movable relative to the body from a retracted position wherein a needle of the syringe is retracted inside the body, to an injection position wherein the needle protrudes outside the body.

15. The apparatus according to claim 14, comprising a syringe barrel and a syringe plunger, wherein operating a plunger of the syringe received inside the hollow body sequentially slides the syringe towards the injection position and then slides the plunger relative to the barrel.

16. The apparatus according to claim 14, wherein the support comprises a bearing surface against which a rim of the syringe can abut, so that operating a plunger of the syringe causes sequentially the syringe to slide relative to the body towards the injection position until the rim of the barrel abut against the bearing surface and then the plunger to slide into the syringe barrel.

17. The apparatus according to claim 14, comprising a releasable connector connecting a syringe plunger and a syringe barrel of the syringe in common sliding movement relative to the body and releasing said connection at a predetermined position of the syringe relative to the body.

18. The apparatus according to claim 17, wherein the releasable connector comprises at least one elastic member prestressed against an inner wall of the body, said inner wall having a housing for accommodating the elastic member when the syringe reaches the predetermined position so as to release the elastic member whereby the plunger is allowed to slide relative to the barrel.

19. The apparatus according to claim 18, wherein the releasable connector comprises a spacer arranged between the syringe barrel and the syringe plunger to prevent sliding movement of the plunger relative to the barrel.

20. The apparatus according to claim 19, wherein the spacer has grooves for receiving fingers of the plunger and the prestressed elastic member is adapted for preventing the fingers from sliding in the grooves until the elastic member is released.

21. The apparatus according to claim 15, comprising a push button for operating the plunger.

22. The apparatus according to claim 13, wherein the support comprises a finger bearing flange projecting outwardly from the body for an operator to retain the support when sliding the syringe relative to the body.

23. The apparatus according to claim 1, comprising a syringe barrel and a syringe needle, wherein the syringe barrel comprises a carpule sealed by a protective cap, the needle being movable rearwards relative to the carpule for simultaneously connecting the needle to the barrel to assemble the syringe and piercing the protective cap with the needle, before moving the assembled syringe towards an injection position.

24. The apparatus according to claim 23, comprising a needle support for supporting the syringe needle, the needle support being operable from outside the body for moving the needle relative to the carpule in order to pierce the protective cap.

25. The apparatus according to claim 23, comprising a removable safety ring for preventing movement of the needle relative to the body.

26. The apparatus according to claim 1, wherein the guide comprises a support having a hollow body, the hollow body comprising a fixed part and a mobile part which can slide relative to the fixed part, the mobile part being adapted for receiving a barrel of a syringe, such that the syringe and the mobile part can move in a common sliding movement relative to the fixed part.

27. The apparatus according to claim 26, comprising a locking member for preventing accidental movement of the mobile part relative to the fixed part.

28. The apparatus according to claim 27, wherein the locking member comprises a locking projection which can be accommodated in a locking recess, the apparatus comprising means for removing the locking projection from the locking recess, whereby allowing movement of the mobile part relative to the fixed part.

29. The apparatus according to claim 26, wherein the mobile part surrounds the fixed part.

30. The apparatus according to claim 26, comprising a rubbing member which generates friction between the fixed part and the mobile part thereby slowing down the movement of the mobile part relative to the fixed part.

31. The apparatus according to claim 26, comprising a resilient member arranged between a plunger of the syringe and the mobile part, the resilient member being adapted for exerting a restoring force which goes against a sliding movement of the plunger relative to the barrel of the syringe.

32. The apparatus according to claim 31, wherein operating the mobile part sequentially causes the mobile part to slide relative to the fixed part and then the plunger to slide relative to the barrel.

33. The apparatus according to claim 26, comprising a resilient member arranged between the fixed part and the mobile part, the resilient member being adapted for exerting a restoring force which goes against a sliding movement of the mobile part relative to the fixed part.

34. The apparatus according to claim 33, wherein operating a plunger of the syringe sequentially slides the mobile part relative to the fixed part until the restoring force reaches a predetermined limit and then slides the plunger relative to the barrel.

35. The apparatus according to claim 31, wherein the resilient member exerts a restoring force which causes the syringe to spontaneously retract into the hollow body after injection.

\* \* \* \* \*